US009597210B2

(12) United States Patent
McDermott et al.

(10) Patent No.: US 9,597,210 B2
(45) Date of Patent: Mar. 21, 2017

(54) DRUG DELIVERY SYSTEM

(71) Applicant: C. R. Bard, Inc., Murray Hill, NJ (US)

(72) Inventors: John D. McDermott, Chandler, AZ (US); Alexander W. Tessmer, Phoenix, AZ (US); David G. Spilka, Phoenix, AZ (US)

(73) Assignee: C. R. Bard, Inc., Murray Hill, NJ (US)

(*) Notice: Subject to any disclaimer, the term of this patent is extended or adjusted under 35 U.S.C. 154(b) by 301 days.

(21) Appl. No.: 14/309,292

(22) Filed: Jun. 19, 2014

(65) Prior Publication Data

US 2014/0303706 A1 Oct. 9, 2014

Related U.S. Application Data

(62) Division of application No. 13/524,797, filed on Jun. 15, 2012, now Pat. No. 8,758,293, which is a division of application No. 11/994,294, filed as application No. PCT/US2006/026786 on Jul. 7, 2016, now Pat. No. 8,206,348.

(60) Provisional application No. 60/697,649, filed on Jul. 8, 2005.

(51) Int. Cl.

| | |
|---|---|
| ***A61F 2/95*** | (2013.01) |
| ***A61F 2/86*** | (2013.01) |
| *A61F 2/01* | (2006.01) |

(52) U.S. Cl.

CPC .................. *A61F 2/86* (2013.01); *A61F 2/95* (2013.01); *A61F 2/01* (2013.01); *A61F 2250/0067* (2013.01); *A61F 2250/0068* (2013.01)

(58) Field of Classification Search

CPC ................ A61F 2250/0067; A61F 2/95; A61F 2250/0068; A61F 2/86; A61M 2025/105

See application file for complete search history.

(56) References Cited

U.S. PATENT DOCUMENTS

| | | | | |
|---|---|---|---|---|
| 5,102,402 | A * | 4/1992 | Dror | A61F 2/958 604/103.02 |
| 5,282,785 | A * | 2/1994 | Shapland | A61M 25/104 604/103.01 |
| 5,439,446 | A | 8/1995 | Barry | |

(Continued)

FOREIGN PATENT DOCUMENTS

| | | |
|---|---|---|
| JP | 2004-049586 A | 2/2004 |
| JP | 2007-530278 A | 11/2007 |

(Continued)

OTHER PUBLICATIONS

EP 06786817.4 Examination Report dated Apr. 29, 2013.

(Continued)

*Primary Examiner* — Aarti B Berdichevsky

(74) *Attorney, Agent, or Firm* — Rutan & Tucker, LLP

(57) ABSTRACT

Apparatuses and methods for coating and/or loading a medical device with a therapeutic agent prior to or during the placement of the medical device within the patient's body. In one variation, the medical device is coated and/or loaded with a therapeutic agent while the device is positioned in a delivery apparatus. In another variation, the delivery apparatus comprises a reservoir for retaining a therapeutic agent. The user may release the therapeutic agent from the reservoir prior to or during the placement of the device to coat and/or load the device with the therapeutic agent.

16 Claims, 8 Drawing Sheets

(56) References Cited

U.S. PATENT DOCUMENTS

| | | | | |
|---|---|---|---|---|
| 5,685,847 | A | 11/1997 | Barry | |
| 5,697,967 | A | 12/1997 | Dinh et al. | |
| 5,755,722 | A | 5/1998 | Barry et al. | |
| 5,807,306 | A * | 9/1998 | Shapland | A61M 25/104 604/21 |
| 5,857,998 | A | 1/1999 | Barry | |
| 5,882,335 | A | 3/1999 | Leone et al. | |
| 5,954,693 | A | 9/1999 | Barry | |
| 6,197,013 | B1 | 3/2001 | Reed et al. | |
| 6,344,028 | B1 | 2/2002 | Barry | |
| 6,364,856 | B1 | 4/2002 | Ding et al. | |
| 6,613,084 | B2 | 9/2003 | Yang | |
| 6,656,162 | B2 | 12/2003 | Santini, Jr. et al. | |
| 6,663,590 | B2 | 12/2003 | Blatter | |
| 6,699,282 | B1 | 3/2004 | Sceusa | |
| 6,949,114 | B2 | 9/2005 | Milo et al. | |
| 7,048,962 | B2 | 5/2006 | Shekalim et al. | |
| 8,206,348 | B2 | 6/2012 | McDermott et al. | |
| 2002/0077592 | A1 | 6/2002 | Barry | |
| 2004/0002715 | A1* | 1/2004 | McDermott | A61F 2/07 606/108 |
| 2004/0002754 | A1* | 1/2004 | McDermott | A61F 2/07 623/1.23 |
| 2004/0010309 | A1 | 1/2004 | Seward et al. | |
| 2005/0038504 | A1 | 2/2005 | Halleriet et al. | |
| 2006/0085054 | A1 | 4/2006 | Zikorus et al. | |
| 2009/0105686 | A1* | 4/2009 | Snow | A61F 2/958 604/509 |
| 2012/0259290 | A1 | 10/2012 | McDermott et al. | |

FOREIGN PATENT DOCUMENTS

| | | | |
|---|---|---|---|
| JP | 5090346 | | 9/2012 |
| WO | 03045275 | A2 | 6/2003 |
| WO | 2006028821 | A1 | 3/2006 |
| WO | 2007008829 | A2 | 1/2007 |

OTHER PUBLICATIONS

EP 13150963.0 Extended European Search Report dated May 2, 2013.

JP 2008-520444 filed Jul. 7, 2006 Office Action dated Feb. 22, 2012.

JP 2008-520444 filed Jul. 7, 2006 Office Action dated Jul. 13, 2011.

PCT/US2006/026786 filed Jul. 7, 2006 International Preliminary Report on Patentability dated Mar. 17, 2009 and Written Opinion dated Dec. 10, 2007.

PCT/US2006/026786 filed Jul. 7, 2006 International Search Report dated Dec. 10, 2007.

U.S. Appl. No. 11/994,294, filed Dec. 28, 2007 Advisory Action dated Jan. 10, 2012.

U.S. Appl. No. 11/994,294, filed Dec. 28, 2007 Final Office Action dated Oct. 27, 2011.

U.S. Appl. No. 11/994,294, filed Dec. 28, 2007 Non-Final Office Action dated May 31, 2011.

U.S. Appl. No. 11/994,294, filed Dec. 28, 2007 Notice of Allowance dated Mar. 2, 2012.

U.S. Appl. No. 13/524,797, filed Jun. 15, 2012 Non-Final Office Action dated Nov. 1, 2013.

* cited by examiner 2
32
22
24
8
12
MEDICAL DEVICE
10
30
20
16
4
14
18
6

2
40
44
46
38
34
42
36

50
48

2
70
MEDICAL DEVICE
72
64
66
68

60
58
62
30
52
56
54

78
80
76
74

2
92
88
82
4
84
30
86
90

2
96
102
98
104
100
110
106
94
108

2
118
116
30
114
120
112

FIG. 10
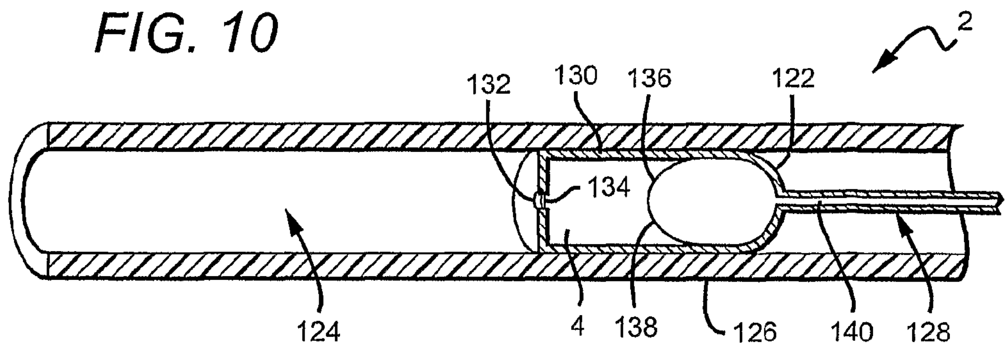
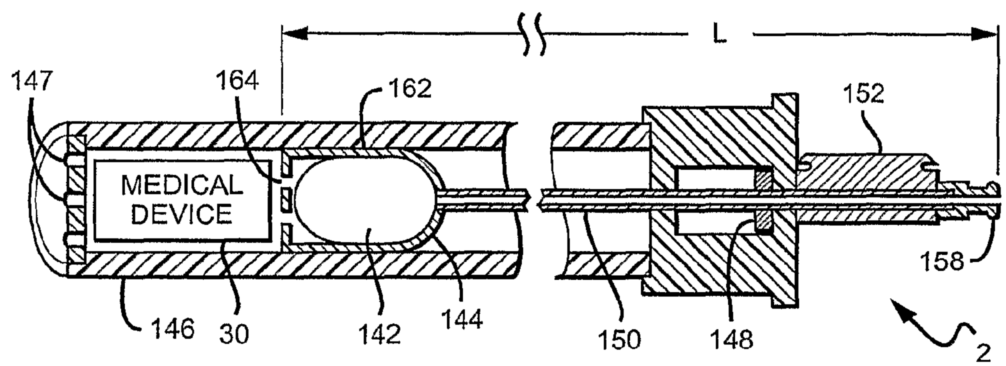
FIG. 11A
FIG. 11B
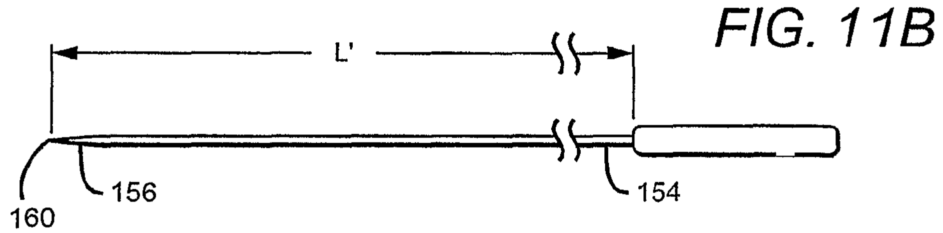
FIG. 12
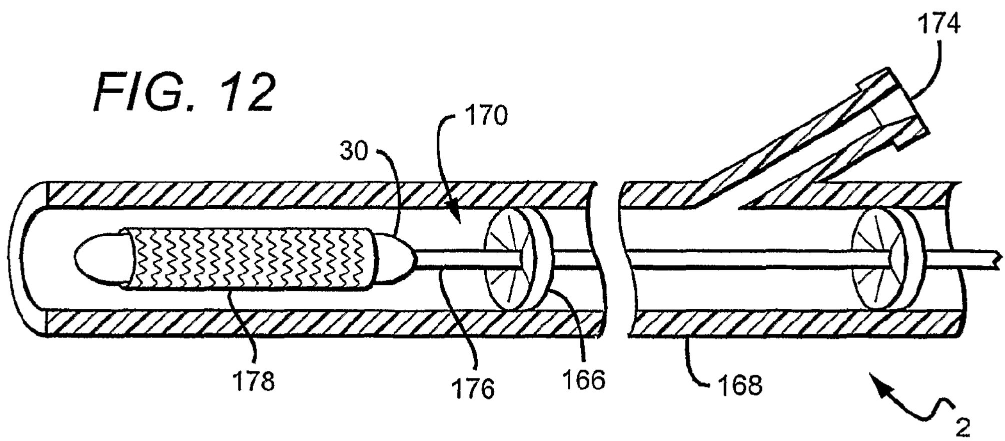

FIG. 17
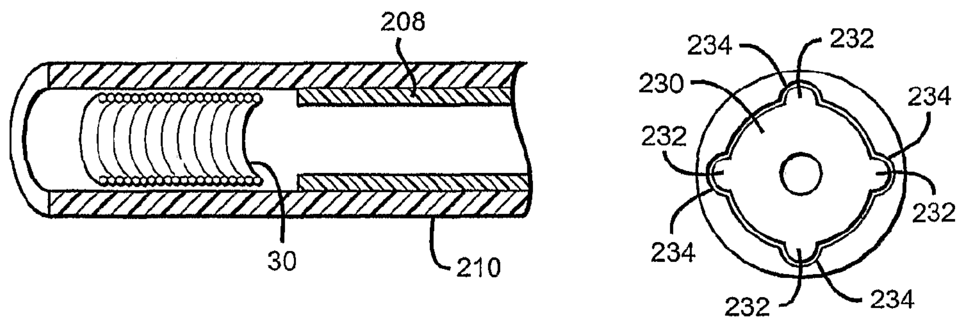
FIG. 19B
FIG. 18
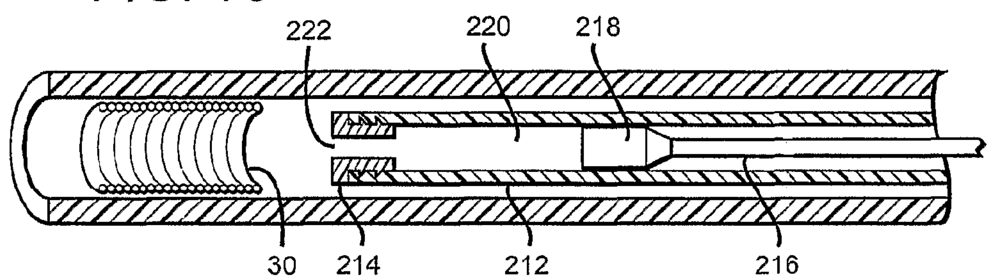
FIG. 19A
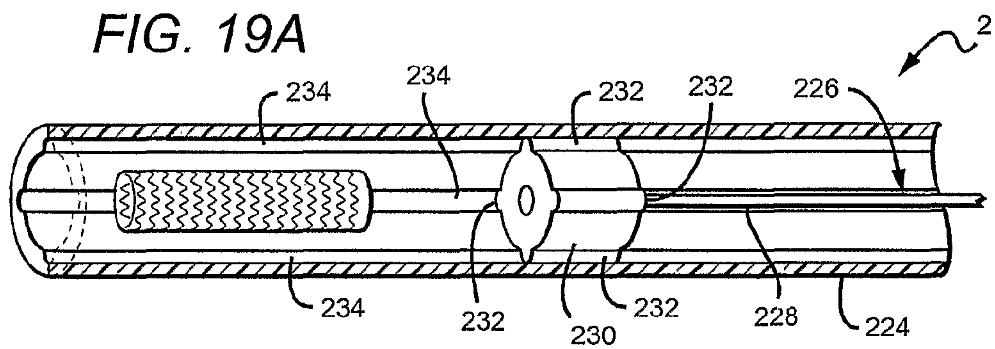
FIG. 20
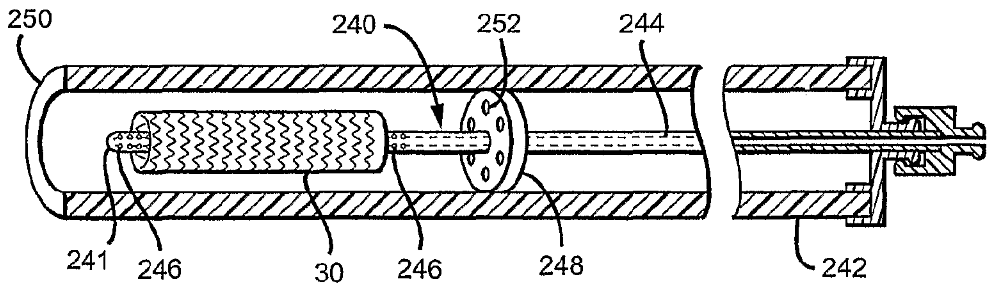

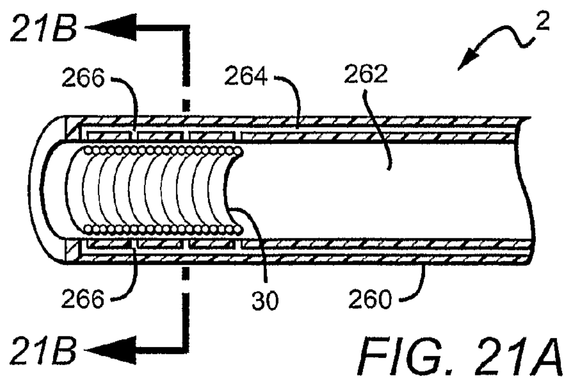
FIG. 21A
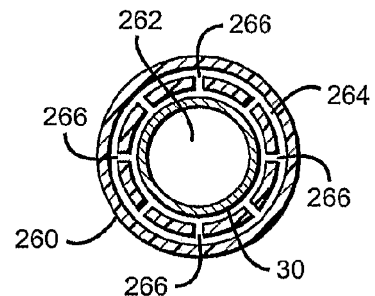
FIG. 21B
FIG. 22
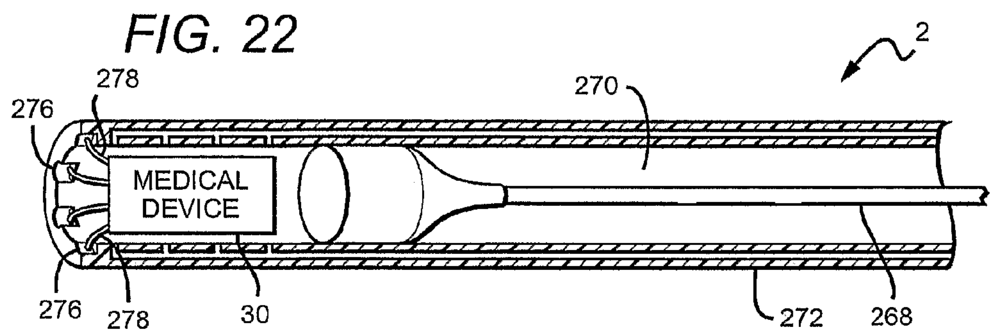
FIG. 23
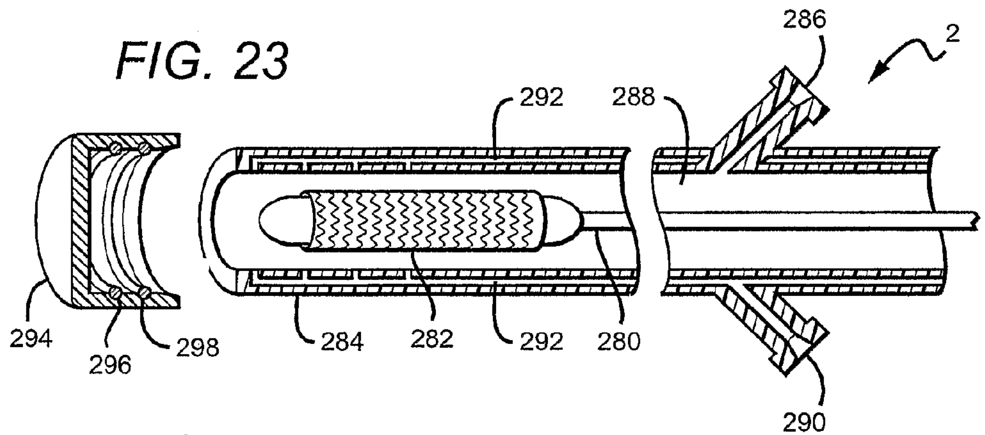
FIG. 24
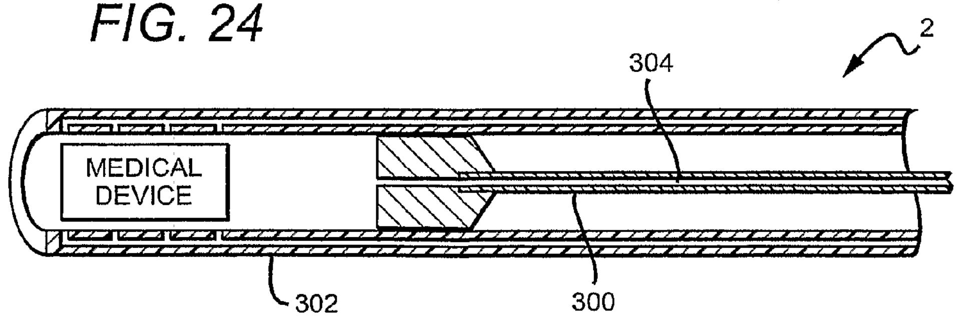

DRUG DELIVERY SYSTEM

PRIORITY

This application is a division of U.S. patent application Ser. No. 13/524,797, filed Jun. 15, 2012, now U.S. Pat. No. 8,758,293, which is a division of U.S. patent application Ser. No. 11/994,294, filed Dec. 28, 2007, now U.S. Pat. No. 8,206,348, which is a U.S. National Stage Application under 35 U.S.C. §371 of International Patent Application No. PCT/US2006/026786, filed Jul. 7, 2006, which claims the benefit under 35 U.S.C. §119(e) to U.S. Provisional Patent Application No. 60/697,649, filed Jul. 8, 2005, each of which is incorporated by reference into this application as if fully set forth herein.

BACKGROUND OF THE INVENTION

The introduction of drug-eluting stents (DES) has been a major advancement in the field of cardiovascular medicine due to the ability of the stents, which are coated with a drug, to prevent restenosis of a vessel. Previous bare metal stents were only able to reduce the rate of restenosis, caused by intimal hyperplasia, to approximately 20-25%. The medicine or drug that is associated with the DES is delivered directly to the blockage site, reducing restenosis rates even further. However, implantable medical devices that are pre-coated with drugs may have a significantly shorter shelf-life than their non-coated counterparts. For example, the potency of the drug may decrease over time, such that the expiration date of the device must take into account the degradation of drug. In addition, viability concerns may prevent one from manufacturing a stent pre-coated with drugs and substances that degenerate within a short period of time at room temperature. For example, drugs, which are based on large molecule biologics (e.g., DNA, protein, monoclonal antibodies, etc.) may be particularly susceptible to degradation, and therefore are difficult to implement as a pre-coated layer on a stent. Furthermore, because most pre-coated devices do not permit the medical practitioner to change or modify the drug associated with the device, the pre-coated devices may limit the medical practitioner's ability to determine and implement the best medication/device combination based on specific treatment needs.

Examples of current drug delivery devices and methods are disclosed in U.S. Patent Application, Publication No. 2004/0010309 A1, titled "METHODS AND SYSTEMS FOR DELIVERING LIQUID SUBSTANCES TO TISSUES SURROUNDING BODY LUMENS" by Seward et al., published Jan. 15, 2004; U.S. Pat. No. 6,699,282 B1 titled "METHOD AND APPARATUS FOR DELIVERY OF MEDICATION" issued to Sceusa, dated Mar. 2, 2004; U.S. Pat. No. 6,656,162 B2 titled "IMPLANTABLE DRUG DELIVERY STENTS" issued to Santini, Jr. et al., dated Dec. 2, 2003; U.S. Pat. No. 6,613,084 B2 titled "STENT HAVING COVER WITH DRUG DELIVERY CAPABILITY" issued to Yang, dated Sep. 2, 2003; U.S. Pat. No. 6,344,028 B1 titled "REPLENISHABLE STENT AND DELIVERY SYSTEM" issued to Barry, dated Feb. 5, 2002; U.S. Pat. No. 5,954,693 titled "REPLENISHABLE STENT AND DELIVERY SYSTEM" issued to Barry, dated Sep. 21, 1999; U.S. Pat. No. 5,857,998 titled "STENT AND THERAPEUTIC DELIVERY SYSTEM" issued to Barry, dated Jan. 12, 1999; U.S. Pat. No. 5,755,722 titled "STENT PLACEMENT DEVICE WITH MEDICATION DISPENSER AND METHOD" issued to Barry et al., dated May 26, 1998; U.S. Pat. No. 5,685,847 titled "STENT AND THERAPEUTIC SYSTEM" issued to Barry, dated Nov. 11, 1997; and U.S. Pat. No. 5,439,446 titled "STENT AND THERAPEUTIC SYSTEM" issued to Barry, dated Aug. 8, 1995; each of which is incorporated herein by reference in its entirety.

SUMMARY OF THE INVENTION

Disclosed herein are various apparatuses and methods for loading and/or coating a medical device (e.g., stents, stent grafts, endovascular grafts, vascular filters, etc.) with a therapeutic agent (e.g., drugs, pharmaceuticals, antithrombogenic agents, anti-inflammatory agents, antibacterial agents, anti-viral agents, biologics, DNAs, RNAs, viral vectors, monoclonal antibodies, growth factors, cells, stem cells, cartilage scaffolds, etc.) immediately prior to or during the placement of the medical device within a patient's body. In one variation, the delivery apparatus is configured such that a medical device, loaded in the delivery apparatus, can be coated or infused with a therapeutic agent while the medical device is positioned in the delivery apparatus. In another variation, the delivery apparatus is configured such that a medical device housed in the delivery apparatus is coated or infused with a therapeutic agent as the medical device is being ejected out of the delivery apparatus and into the patient's body. In yet another variation, the delivery apparatus is configured to simultaneously deliver a medical device and a therapeutic agent into a treatment area within the patient's body.

For example, the delivery apparatus may include a reservoir for holding a drug. The user can release the drug from the reservoir to coat a medical device loaded in the delivery apparatus prior to or during the insertion of the delivery apparatus into the patient's body. In another example, a capsule containing a therapeutic agent is positioned in the distal portion of the delivery apparatus. The user can break the capsule and release the therapeutic agent to infuse or cover the medical device secured in the delivery apparatus whenever he or she is ready to do so. The capsule may be pressurized to facilitate the distribution of the therapeutic agent in the distal portion of the delivery apparatus.

In another example, the delivery apparatus includes a chamber at the distal portion of the apparatus for housing the medical device. A suction mechanism is provided in the delivery apparatus to draw a therapeutic agent, in the form of liquid or gel, into the chamber to coat and/or load the medical device. In one variation, the suction mechanism is positioned within the body of the apparatus. A negative pressure is generated by the suction mechanism, which results in the therapeutic agent positioned at the distal opening of the delivery apparatus entering the apparatus due to the surrounding atmospheric pressure. In one particular design, the delivery apparatus includes a catheter and a slidable insert forming a seal against the catheter lumen wall. As the insert is displaced proximally relative to the catheter, suction is generated in the lumen of the catheter, and the therapeutic agent positioned at the distal opening of the catheter is drawn into the catheter lumen. As the therapeutic agent fills the distal portion of the catheter lumen, the medical device disposed therein is coated and/or loaded with the therapeutic agent. In another variation, a suction mechanism is coupled to the proximal end of the delivery apparatus. A medical device is disposed in a distally positioned chamber in the delivery apparatus. The distal chamber housing the medical device is in fluid communication with the suction mechanism. This fluid communication may be established through a channel extending from the proximal end of the delivery apparatus to the distal end of the delivery apparatus. The suction mechanism generates a negative pressure in the channel to draw the therapeutic agent positioned at the distal end of the delivery apparatus into the distal chamber. As the therapeutic agent enters the distal chamber, the medical device disposed therein is coated and/or loaded with the therapeutic agent.

In another example, the delivery apparatus includes a drug delivery lumen which provides a fluid conduit for infusing a therapeutic agent into a chamber in the distal portion of the apparatus. A medical device housed in the chamber can be coated with a therapeutic agent at the user's discretion. A pressurized foam or mist may be injected into the delivery lumen to coat the medical device prior to or during the implantation process.

In another variation, the delivery apparatus includes a reservoir at the distal end thereof, through which a medical device can be delivered. The user may fill the reservoir with a therapeutic agent, such that when the medical device is delivered therethrough, the medical device is coated with the therapeutic agent. In another design variation, the delivery apparatus includes two lumens in fluid communication with a chamber, which houses a medical device at the distal portion of the delivery apparatus. A therapeutic agent can be injected into the first lumen and extracted through the second lumen, such that a continuous flow of therapeutic agent is delivered over the medical device to coat and/or load the medical device with the therapeutic agent prior to implantation.

In yet another variation, the medical device is coated or infused with a therapeutic agent under pressure, while positioned inside the body of the delivery apparatus, after which the medical device is deployed into the patient's body. For example, an aerospray-can carrying a therapeutic agent can be coupled to the distal end of the delivery apparatus to inject therein the therapeutic agent. The injected therapeutic agent is deposited onto and/or absorbed into the medical device. In another example, the medical practitioner couples a syringe filled with a therapeutic agent onto the distal end of the delivery apparatus, and then injects the therapeutic agent into the lumen of the delivery apparatus by depressing the plunger on the syringe. The tip of the syringe may be configured for insertion into the distal end of the delivery apparatus. In another variation, a universal syringe adaptor may be provided to couple syringe of various sizes to the delivery apparatus. In yet another example, a pressurized drug capsule is attached to the distal end of the delivery apparatus. The user can release the drug from the capsule and infuse the drug into the lumen of the delivery apparatus, which houses the medical device.

Methods for loading, coating or infusing a medical device with a therapeutic agent, while the medical device is disposed in the delivery apparatus, are also disclosed herein. In one approach, the therapeutic agent and the medical device are stored separately. For example, a therapeutic agent comprising biologics, which requires low temperature storage, is placed in a refrigerator, while the delivery apparatus along with a medical device is stored in a cabinet. The medical device may be pre-loaded into the delivery apparatus and provided to the hospital or clinic as an integrated unit. When the medical practitioner is ready to implant the medical device, the therapeutic agent can be infused into the delivery apparatus to coat and/or load the medical device. The medical practitioner may also personally check and ensure that a fresh and active therapeutic agent is loaded into the delivery apparatus. Furthermore, the medical practitioner may be provided with two or more therapeutic substances, from which he or she can elect for loading onto the medical device. In another variation of the method, the therapeutic agent is released onto the intended treatment site as the medical device is being deployed by the delivery apparatus.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 10 illustrates another variation of a delivery apparatus with a reservoir located with a slidable element. The reservoir can be utilized to hold a therapeutic agent. The slidable element may also serve as a pusher for deploying an implantable medical device placed in the distal lumen of the delivery apparatus.

FIG. 11A illustrates another variation of a delivery apparatus with built-in a displacement control mechanism to control the pusher rod. A capsule is positioned within the distal end of the pusher rod to serve as a reservoir for a therapeutic agent.

FIG. 11B illustrates an activation element for use with the delivery apparatus of FIG. 11A. The activation element, when inserted into the proximal end of the pusher rod, allows the user to break the capsule and release the therapeutic agent.

FIG. 12 illustrates another variation of a delivery apparatus including a valve positioned within a catheter to form a chamber at the distal end of the catheter. In this variation, the position of the valve is fixed within the lumen of the catheter.

FIG. 17 illustrates another variation of a delivery apparatus comprising a delivery catheter with a tubing slidably disposed therein. The tubing serves as a mechanism to deploy a medical device. The lumen within the inner slidable tubing serves as a fluid conduit for delivering therapeutic agent to coat/load the medical device while the medical device is positioned within the distal end of the apparatus.

FIG. 18 illustrates another variation of a delivery apparatus comprising a slidable element positioned within the lumen of a catheter for deploying the medical device. The slidable element is configured with a suction mechanism which can be utilized to draw fluids into the distal end of the apparatus.

FIG. 19A illustrates another variation of a delivery apparatus including a pusher pad configured with flanges. The radially extending flanges may assist with engagement of a stent placed within the lumen of the delivery catheter.

FIG. 19B is a frontal view of the delivery apparatus of FIG. 19A, shown without the stent.

FIG. 20 illustrates another variation of a delivery apparatus including a slidable insert configured to distribute a therapeutic agent over a medical device placed within the lumen of the delivery apparatus.

FIG. 21A illustrates another variation of a delivery apparatus comprising a delivery catheter with a first lumen for housing a medical device and a second lumen configured to distribute a therapeutic agent over the medical device. As shown in the example of FIG. 21A, the outer lumen is configured with inner facing orifices to inject the therapeutic agent over the outer circumferential surface of the medical device.

FIG. 21B is a cross-sectional view of the delivery apparatus of FIG. 21A. The cross-section is taken at A-A as shown in FIG. 21A.

FIG. 22 illustrates another dual lumen delivery apparatus configured for deploying a vascular filter. In this particular design, the delivery apparatus is configured with a mechanism (i.e., pusher element) for ejecting the medical device (i.e., vascular filter).

FIG. 23 illustrates yet another dual lumen delivery apparatus design. In this example, a stent is placed over a compressed balloon on a balloon catheter. An optional cap may be provided to allow the user to temporarily seal the distal end of the apparatus while the user coats or loads the stent with a therapeutic agent infused through the elongated lumens of the apparatus.

FIG. 24 illustrates another dual lumen delivery apparatus configured with a pusher element. The pusher element is configured with a lumen for fluid delivery.

Figure 1:
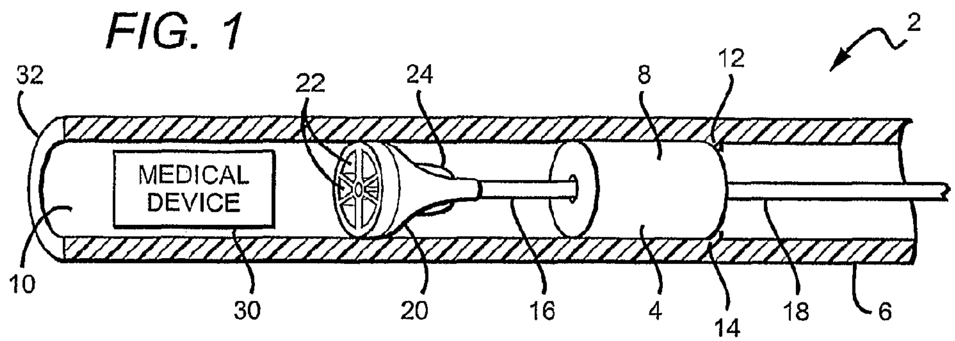
FIG. 1 illustrates one variation of a delivery apparatus comprising a chamber for housing a medical device for delivery and a reservoir for holding a therapeutic agent. In this particular design, a capsule is utilized to contain the therapeutic agent.

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description would enable one skilled in the art to make and use the invention, and describes several embodiments, adaptations, variations, alternatives and uses of the invention, including what is presently believed to be the best mode of carrying out the invention.

Before describing preferred embodiments, it is to be understood that unless otherwise indicated, this invention need not be limited to applications in humans. As one skilled in the art would appreciate, variations of the invention may be applied to other mammals as well. Moreover, it should be understood that embodiments of the present invention may be applied in combination with various catheters, tubing introducers or other implantation and connection devices for placement of a medical device into a patient's body.

DETAILED DESCRIPTION OF THE PREFERRED EMBODIMENTS

Vascular filters, stents and endovascular stent-grafts are used herein as examples of the types of medical devices to be implanted with a delivery apparatus that possesses the integrated capability to deliver a therapeutic agent onto the medical device, in order to illustrate the various aspects of the invention disclosed herein. In light of the disclosure herein, one skilled in the art would appreciate that variations of the delivery apparatus may be utilized for placement of different medical devices, not specifically discussed herein, into a patients' body. Certain variations of the delivery apparatus described in the preferred embodiments of the present invention are particularly useful for pre-loading a medical device with a therapeutic agent prior to insertion of the medical device into the patient's body. Other variations of the delivery apparatus according to the present invention can be configured for simultaneous delivery of a therapeutic agent during the deployment of the medical device. In addition, some variations may support both pre-loading and simultaneous delivery of therapeutic agents.

It must also be noted that, as used in this specification and the appended claims, the singular forms "a," "an" and "the" include plural referents unless the context clearly dictates otherwise. Thus, for example, the term "a chamber" is intended to mean a single chamber or a combination of chambers, "a fluid" is intended to mean one or more fluids, or a mixture thereof. Furthermore, the words "proximal" and "distal" refer to directions closer to and away from, respectively, a medical practitioner operating the apparatus, with the tip end (i.e., distal end) placed inside the patient's body. Thus, for example, a catheter end placed within the body of the patient would be the distal end of the catheter, while the catheter end outside the patient's body would be the proximal end of the catheter.

In one preferred embodiment, the delivery apparatus is configured with a reservoir for containing a therapeutic agent. The therapeutic agent can be released while the medical device is still secure within the delivery apparatus and/or during the placement of the medical device within the patient's body. In one variation, the delivery apparatus includes a chamber for housing the medical device, a reservoir for containing the therapeutic agent, and a mechanism for deploying a medical device from the body of the delivery apparatus. The delivery apparatus may further include the medical device disposed in the chamber of the delivery apparatus.

The drug or therapeutic agent can be one or more bioactive agents. The bio-active agents can include, but are not limited to, vasodilator, anti-coagulants, such as, for example, warfarin and heparin. Other bio-active agents can include, but are not limited to, agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine }); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

FIG. 1 illustrates the example where a delivery apparatus 2 includes a reservoir 4 containing a therapeutic agent. In this particular design, the delivery apparatus 2 includes an elongated catheter 6 and a capsule 8 positioned in the distal portion of the catheter lumen 10. The capsule 8 serves as a reservoir for holding a therapeutic agent. Optional ledges 12, 14 are provided on the catheter lumen wall to prevent the capsule 8 from displacing in the proximal direction. In one variation, the capsule 8 includes a polymeric material. A pusher element 16 is slidably positioned within the lumen of the catheter. The pusher element 16 includes a flexible rod extending through a central lumen of the capsule 8 and a pusher pad 20 attached to the distal end of the flexible rod 18. The pusher pad 20 is configured with a plurality of channels 22, such that fluids may flow from the proximal side of the pusher pad towards the distal side of the pusher pad. Raised profiles 24 are provided on the proximal side of the pusher pad for engaging the capsule 8 and releasing the therapeutic agent from the capsule. In one variation, the raised profiles 24 include a plurality of sharp edges that can cut into the distal end of the capsule 8 to break open the capsule and release the therapeutic agent contained therein. A medical device 30, such as a vascular filter, ca be positioned in the lumen at the distal end 32 of the catheter 6.

To release the therapeutic agent from the capsule 8, the pusher element 16 is displaced in the proximal direction to break the capsule 8. Once the capsule is broken, the therapeutic agent flows out of the capsule and infuses the distal portion of the catheter lumen. In one variation, the compartment within the capsule is pressurized to facilitate the dispersion of the therapeutic agent when the integrity of the capsule is compromised. The therapeutic agent flows over the vessel filter and coats the vessel filter with a layer of therapeutic agent. In one variation, the therapeutic agent includes a gel, and in another variation, the therapeutic agent includes a liquid.

As discussed herein, various other medical devices, such as for example stents, grafts, stent-grafts, etc., can be placed in the lumen of this catheter for delivery into a patient's body. In one variation, the medical device includes an absorbing component for retaining a portion of the therapeutic agent that flows over the medical device. After the medical device has been implanted, the absorbing component will release the therapeutic agent to the implantation site over a period of time. For example, a porous polymer layer may be incorporated on the medical device to retain the therapeutic agent. Once the medical device 30 is loaded and/or coated with the therapeutic agent, the user can advance the pusher element 16 to eject the medical device out of the distal end 32 of the catheter 6. In one approach, the user can release the capsule and coat and/or load the medical device prior to inserting the catheter into the patient's body. Once the catheter is inserted into the patient's body, the pusher wire can be advanced distally to deploy the medical device. In another approach, the catheter is inserted into the patient's body first. Once the catheter is positioned in the desired location, the capsule with the therapeutic agent is released, followed by the deployment of the medical device. In another variation, a locking mechanism is provided at the proximal end of the delivery apparatus to lock the deploying mechanism (e.g., pusher element) in position while the apparatus is being transported, in order to prevent accidental release of the therapeutic agent and/or accidental ejection of the medical device.

Figure 2:
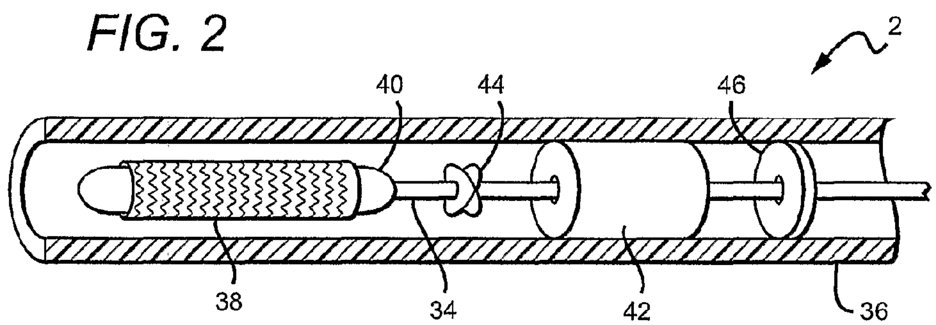
FIG. 2 illustrates another variation of a delivery apparatus including a capsule for containing a therapeutic agent.

Referring to FIG. 2, another example of a medical device delivery apparatus 2 is illustrated. In this example, a balloon catheter 34 is slidably positioned within the lumen of a delivery catheter 36. A stent 38 is positioned over the compressed balloon 40 at the distal end of the balloon catheter 34. A capsule 42 is positioned within the catheter lumen proximal of the balloon 40 on the balloon catheter 34. An activation element 44 is coupled to the shaft of the balloon catheter 34 for releasing the therapeutic agent from the capsule 42. A separator 46 is positioned on the shaft of the balloon catheter 36 proximal of the capsule 42. The separator 46 keeps the released therapeutic agent in the proximal portion of the catheter. In one variation, the separator includes a stopper, coupled to the shaft of the balloon catheter, as shown in FIG. 2. In another variation the separator includes a seal. In yet another variation, the separator include a one-way valve, which permits fluid flow in the distal direction but not the proximal direction. The valve may allow the user to purge the air from the lumen of the catheter by injecting a liquid into the proximal end of the delivery catheter. Once the catheter lumen is filled with the liquid, the user can release the therapeutic agent from the capsule. The released therapeutic agent displaces the liquid at the distal portion of the catheter lumen proximal of the valve. The valve prevents or minimizes the therapeutic agent from dispersion in the proximal direction. Although a separator 46 has been shown and described, the apparatus 2 can be provided without such a separator.

To release the therapeutic agent, the balloon catheter 34 is displaced in the proximal direction, which causes the activation element 44 to engage the capsule and release the therapeutic agent. The released therapeutic agent flows distally to coat and/or load the stent 38. In one variation, the stent includes a polymeric covering that absorbs and/or binds the therapeutic agent. After the stent has been implanted, the polymeric covering releases the therapeutic agent over time at the implantation site.

Figure 3:
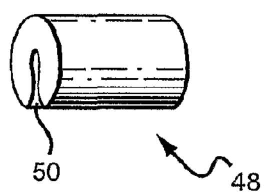
FIG. 3 illustrates one variation of a capsule, which can be removably inserted into a delivery apparatus.

In one variation, the reservoir containing the therapeutic agent is an integral part of the delivery apparatus. In another variation, the reservoir containing the therapeutic agent includes an independent unit that can be removed or detached from the delivery apparatus. FIG. 3 illustrates a detachable capsule 48 that can be coupled onto the shaft of a pusher element or a balloon catheter. The capsule 48 includes a lateral opening/slot 50 on the circumferential surface of the capsule 48, such that the capsule can be clipped onto a shaft through the lateral opening.

In another embodiment, the medical device apparatus includes an elongated catheter and a deployment element slidably positioned within the lumen of the catheter. A stopper is positioned on the deployment element, such that axial displacement of the deployment element creates a negative pressure, which enables suction of a liquid or gel containing a therapeutic agent into the distal lumen of the catheter.

Figure 4:
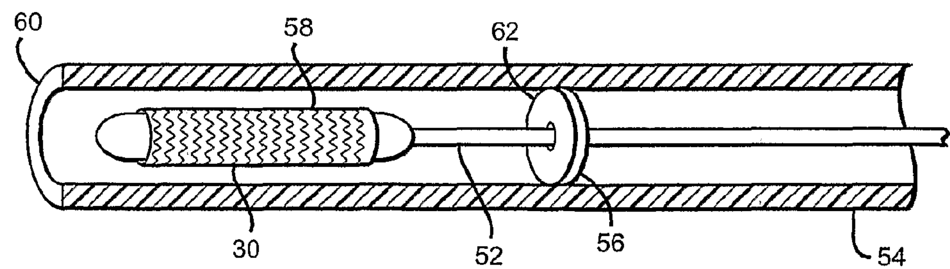
FIG. 4 illustrates another variation of a delivery apparatus including a built-in stopper to allow the user to extract a liquid/gel carrying a therapeutic agent into a distal chamber, which houses a medical device for deployment.

FIG. 4 illustrates this embodiment, in which a balloon catheter 52 positioned within the lumen of a delivery catheter 54 includes a stopper 56 coupled to the shaft of the balloon catheter 52. A medical device, e.g., a stent 58, is loaded on the balloon catheter 52. As the stopper 56 is displaced distally and then withdrawn in the proximal direction, suction is created within the distal portion of the catheter lumen and a liquid or gel carrying a therapeutic agent can be drawn into the distal portion of the catheter lumen to coat and/or load the stent with the therapeutic agent. The stopper 56 can be constructed to move independently of the medical device. In another approach, the therapeutic agent can be injected into the lumen of the catheter through the distal end 60 of the catheter 54. In this approach, a separator (e.g., stopper) keeps at least a substantial portion of the injected therapeutic agent at the distal portion of the catheter lumen. In another variation (not shown), a syringe with a needle is utilized to infuse the distal portion of the lumen with a therapeutic agent. The needle is inserted into the distal end of the catheter and extends past the loaded medical device, such that a gel or liquid therapeutic agent is injected proximal of the medical device. Once the therapeutic agent fills the area between the medical device 30 and the separator 62, further injection of the needle/syringe forces the therapeutic agent to migrate distally to coat the medical device with the therapeutic agent. In yet another variation, another lumen can be provided to delivery a suitable bio-active material to an area proximate the medical device. In this variation, the lumen is couple to a syringe on the proximate end of the delivery mechanism.

Figure 5:
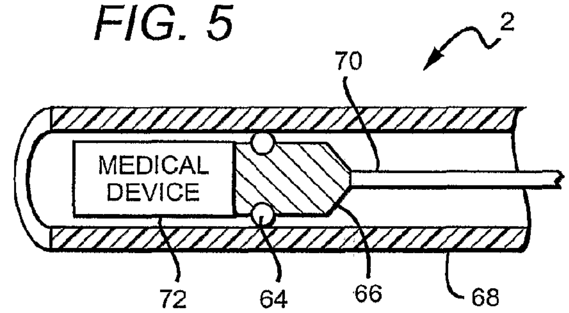
FIG. 5 illustrates another variation of a delivery apparatus configured with a chamber for housing an implantable medical device for deployment. The chamber is also configured for receiving a therapeutic agent to coat/load the medical device.

FIG. 5 illustrates another example, in which an O-ring 64 is placed around a pusher pad 66, such that the user can draw fluids into the distal lumen of the catheter 68 by displacing the pusher element 70 in a proximal direction of the delivery apparatus 2. In this example, a medical device 72 (e.g., as a vascular filter, etc.) is positioned in the distal lumen of the catheter for deployment. In one variation, a suitable guidewire or mechanism can be used to prevent movement of the medical device 72 relative to the catheter 68.

Figure 6:
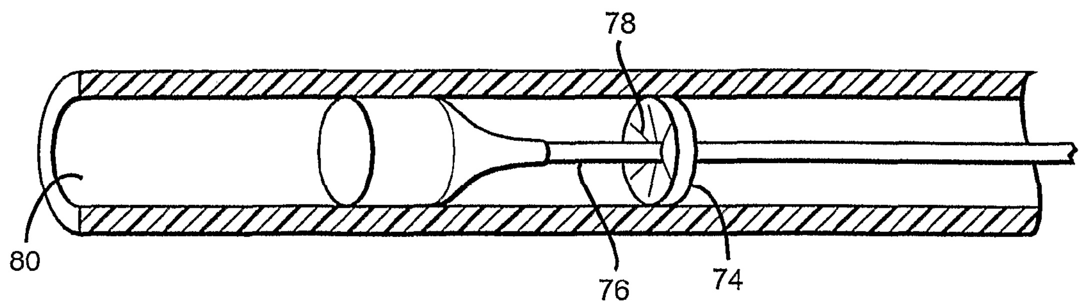
FIG. 6 illustrates another variation of a delivery apparatus with a valve positioned within the lumen of a catheter to form a chamber at the distal portion of the catheter. In this variation, the position of the valve can be displaced within the lumen of the catheter.

FIG. 6 illustrates another variation, in which a polymeric disk 74 is positioned over the shaft of a pusher rod 76 to serve as a separator. The polymeric disk 74 is configured with a plurality of slits 78, such that it can act as a unidirectional valve to permit fluids infused through proximal end of the catheter to travel past the polymeric disk 74 and into the distal portion of the catheter lumen 80, but essentially prevent its flow back proximally. The separator along with the wall of the catheter forms a chamber at the distal end of the catheter for housing a medical device for deployment. Once the medical device is loaded in the distal end of the catheter, a suitable therapeutic agent can be infused/injected into the distal end of the catheter to coat and/or load the catheter with the therapeutic agent. In one approach, saline is first injected into the proximal end of the catheter to displace the air within the lumen of the catheter. A therapeutic agent is then injected through the distal opening to displace the saline within the distal portion of the catheter lumen. In another approach, a liquid therapeutic agent is injected directly into the proximal end of the catheter to fill both the proximal portion and the distal portion of the catheter lumen.

Figure 7:
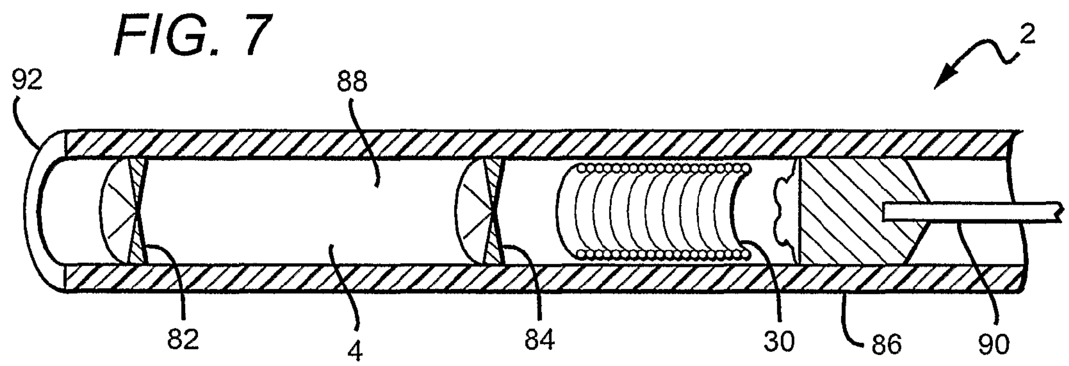
FIG. 7 illustrates another variation of a delivery apparatus including a reservoir at the distal end thereof, through which a medical device can be delivered.

In another aspect, the delivery apparatus 2 includes a reservoir 4 at the distal end thereof, through which a medical device 30 can be delivered. FIG. 7 illustrates one example where two valves 82, 84 are positioned within the lumen of a catheter 86 to form a chamber 88. The valves 82, 84 can be bi-directional valves. In a variation, uni-directional valves can also be implemented. The chamber 88 serves as a reservoir to hold a therapeutic agent. In one variation, each of the valves 82, 84 includes a polymeric slit valve. In the particular example shown in FIG. 7, each of the valves 82, 84 includes a polymeric disk including a plurality of slits. The valves 82, 84 can be configured segmented slits such that that the valves can deform in one direction but not in the opposite direction. Prior to the delivery of the medical device 30, a therapeutic agent is injected into the chamber 88. In one variation, the therapeutic agent is carried in a liquid substance. In another variation, the therapeutic agent is carried in a gel-like substance. To deploy the medical device, the user advances the pusher element 90 distally and forces the medical device 30, through the valve 84, into the chamber 88 filled with the therapeutic agent. The catheter 86 is then inserted into the patient's body. Once the catheter 86 is in position, the medical device 30 is pushed through the distal valve 82 and ejected out of the catheter for deployment within the patient's body. In another approach, the delivery apparatus is inserted into the patient's body while the medical device is still positioned proximal of the chamber 88. Once the catheter is positioned in place, the medical device 30 is advanced distally through the chamber 88 and out the distal end 92 of the delivery apparatus 2. As the medical device 30 passes through the chamber 88, the medical device 30 is coated with the therapeutic agent.

In another variation, the delivery apparatus includes an elongated body including a chamber at the distal portion of the elongated body. The chamber is configured to hold a medical device for delivery into a patient's body. While the device is inside the chamber, the user can infuse the chamber with a therapeutic agent to coat and/or to load the medical device with the therapeutic agent. In one approach, the therapeutic agent is loaded into the chamber while the catheter is still outside the patient's body. In another approach, the therapeutic agent is loaded into the chamber after the delivery apparatus has been inserted into a patient's body.

Figure 8:
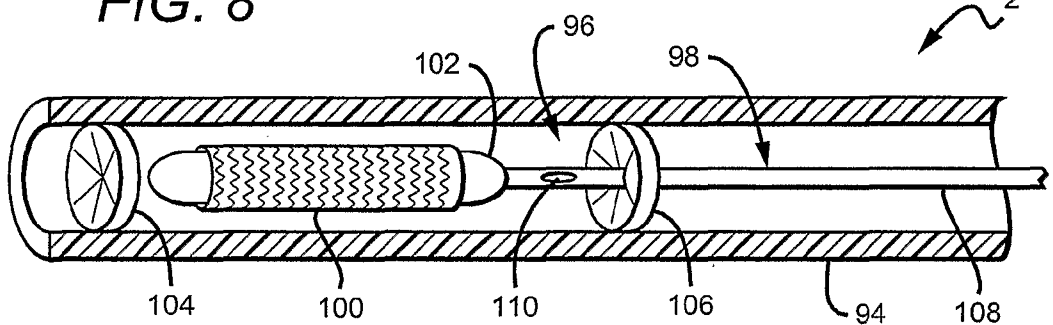
FIG. 8 illustrates another variation of a delivery apparatus including a chamber in which a medical device can be coated/loaded with a therapeutic agent prior to delivery into a patient's body.

FIG. 8 illustrates another example where a delivery apparatus 2 includes an elongated catheter 94 with a chamber 96 positioned within the distal end of the elongated catheter 94. A balloon catheter 98 carrying a medical device, such as for example a stent 100, is slidably positioned in the lumen of the elongated catheter 94. The stent 100 along with the balloon 102 on the balloon catheter 98 is positioned in the distal chamber 96. The chamber 96 is formed with a valve 104 and a separator 106 (e.g., seal, valve, etc.) positioned within the lumen of the catheter 96. The medical device 100 can be placed in the catheter 94 with the medical device positioned distal of the valve 106. In one variation, the chamber 96 is loaded with a therapeutic agent by inserting a needle on a syringe through the distal valve 104 and injecting a therapeutic agent into the chamber 96. In another variation, the shaft 108 of the balloon catheter includes two lumens. A first lumen is utilized to inflate and deflate the balloon 102, while a second lumen in conjunction with port 110 can be utilized to inject a therapeutic agent into the distal chamber 96 within the catheter 94. The therapeutic agent is injected into the second lumen at the proximal end of the balloon catheter. The therapeutic agent then travels down the length of the balloon catheter 98, and exits port 110, which is located close to the balloon 102 at the proximal portion of the catheter shaft 98, and into the chamber 96. Once the stent 100 is coated and/or loaded with the therapeutic agent, the stent 100 can be deployed by advancing the balloon 102 on the balloon catheter 98 out of the catheter 94, and dilating balloon 102 to expand the stent 100.

Figure 9:
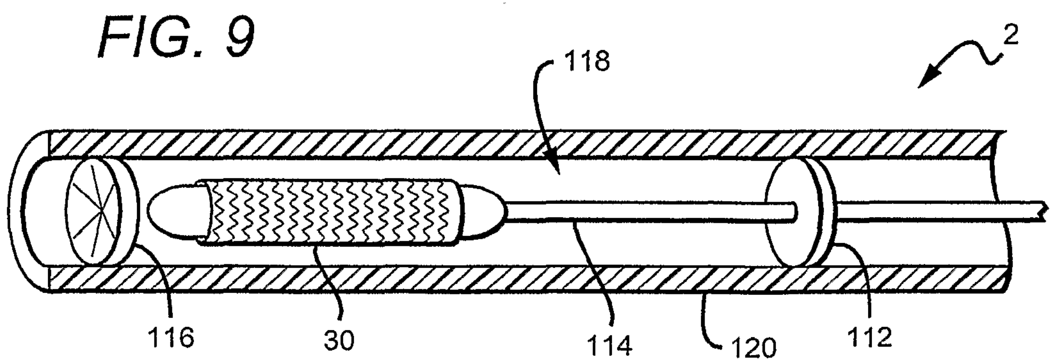
FIG. 9 illustrates another variation of a delivery apparatus including a stopper and a valve to form a chamber for coating/loading the medical device with a therapeutic agent prior to deployment of the medical device.

In another example, the delivery apparatus 2 includes a stopper 112 attached to the shaft of a balloon catheter 114 as shown in FIG. 9. The stopper 112, along with a valve 116 positioned within the distal end of the catheter, forms a chamber 118 when the balloon catheter 114 is retracted within the lumen of the delivery catheter 120. In one variation, the user can infuse the chamber with a therapeutic agent to coat and/or load the medical device 30 (e.g., stent, vascular graft, etc.) positioned on the balloon catheter 114 through the distal end of the catheter. The infusion can be accomplished by a separate lumen and port 110, or by a neele through the distal end, or by filing the catheter with therapeutic agent prior to insertion of the device 30. In another variation, the shaft of the balloon catheter includes a channel to allow the user to infuse the chamber with a therapeutic agent by injecting the therapeutic agent through the distal end of the balloon catheter. In yet another variation, the delivery catheter is configured with a second lumen, such that therapeutic agent can be injected into the chamber through the proximal end of the delivery catheter.

In another aspect, the delivery apparatus 2 includes a medical device deploying mechanism 122. The medical device deploying mechanism is integrated with a reservoir 4 for holding a therapeutic agent for deployment into the lumen of the delivery apparatus. The therapeutic agent can be released into a chamber 124, which holds a medical device, to coat and/or load the medical device with the therapeutic agent. In one variation the deploying mechanism 122 is slidably positioned within a lumen in the delivery apparatus 2.

FIG. 10 illustrates one example, where the delivery apparatus 2 includes an elongated catheter 126 and a pusher element 128 slidably disposed within the lumen of the elongated catheter 126. The distal portion of the pusher element 128 includes a chamber 130 for containing a therapeutic agent. The distal end of the chamber 130 includes an orifice 132 for releasing the therapeutic agent into the lumen of the catheter 126. In one variation, a valve 134 (e.g., a polymeric slit valve, etc.) is positioned over the orifice 132. A displacement mechanism 136 is placed within the chamber 130 to allow the user to control the release of the therapeutic agent from the chamber 130. In the particular example shown in FIG. 10, a balloon/diaphragm 138 is positioned at the proximal end of the chamber 130. The shaft of the pusher element 128 includes a lumen 140 in fluid communication with the balloon/diaphragm 138, such that the user can inject a fluid into the proximal end of the pusher element to inflate the balloon and force the therapeutic agent out the orifice at the distal end of the chamber. The valve 134 can be a check valve with a suitable break pressure rating to prevent premature deployment of the therapeutic agent outside of the reservoir.

In yet another variation, the valve 134 can be eliminated with the expandable member 138 inflated to occupy a substantial volume of the chamber. Deflation of member 138 can be used to generate suction of fluid (gas or liquid or a combination thereof) through orifice 132. Subsequent expansion of the member 138 can be utilized to eject the suctioned fluid.

FIG. 11A illustrates another example, where a capsule 142 is positioned within the chamber of the pusher element 144. A medical device 30 (e.g., a vascular filter, stent, etc.) is disposed in the lumen at the distal end of the catheter 146. A stop 148 is coupled to the shaft 150 of the pusher element 144 to constrain the amount of the pusher element's displacement in the axial direction. A locking clip 152 is placed over the proximal shaft of the pusher element to prevent accidental deployment of the medical device 30. An activation mechanism is provided for releasing the therapeutic agent contained in the capsule 142. In this particular design, the activation mechanism includes an elongated wire 154 with a tapered distal end 156, as shown in FIG. 11B. The elongated wire 154 can be inserted into the proximal end 158 of the pusher element 144 and down the lumen in the shaft 150. As the distal end 160 of the elongated wire 154 passes through the chamber 162, the elongated wire punctures the capsule 142 and releases the therapeutic agent contained therein. In one variation, the compartment within the capsule is pressurizes such that once the integrity of the capsule has been compromised, the therapeutic agent is forced out of the capsule due to the pressure. In such a configuration, a suitable seal may be utilized to prevent flow of the therapeutic agent towards the proximal end. The seal can be, an elastomeric seal positioned between the wire 154 and the lumen 140, or by a suitable tolerance fit between the lumen 140 and wire 154 without the use of an elastomeric seal. The released therapeutic agent exits the orifices 164 at the distal end of the chamber 162 coats and/or loads the medical device 30 with the therapeutic agent. Once the medical device 30 has been coated and/or loaded with the therapeutic agent, the user can remove the locking clip 152 and advance the pusher element 144 distally to eject the medical device 30 out of the delivery apparatus 2. Slots 147, may be provided on the inner lumen of the delivery catheter 146 for holding the medical device 30. For example, slots 147 may be configured to interact with the medical device 30 to prevent the medical device 30 from rotating with the lumen of the delivery catheter 146. In another variation, slots 147 are configured to guide the movement of the medical device 30 as the medical device is being pushed out of the lumen of the delivery catheter 146. In yet another variation, slots 147 are provided to prevent appendages from the medical deice 30 from interfering with the deployment of the medical device.

In another aspect, the delivery apparatus includes a lumen configured for delivering a therapeutic agent into a chamber that houses a medical device for deployment inside a patient's body. A pressurized liquid or gel carrying the therapeutic agent may be transported through the drug delivery lumen down the shaft of the delivery apparatus to coat and/or load the medical device housed in the distal portion of the delivery apparatus.

In one example, as shown in FIG. 12, a separator 166 (e.g., valve, seal, etc.) is positioned within the lumen of a delivery catheter 168 to form a chamber 170 at the distal portion of the delivery catheter. Once the medical device 30 is loaded within the chamber 170, a therapeutic agent can be injected into the chamber 170 to coat the medical device with a therapeutic agent. In one variation, the separator 166 includes a unidirectional valve. Saline is injected into the lumen of the catheter 168 through the proximal side port 174 to purge air out of the lumen of the catheter. As the saline travels down the shaft of the delivery apparatus, the separator 166 is pushed open and the chamber 170 at the distal portion of the delivery apparatus 2 is filled with saline. Next, the user injects a therapeutic agent into the chamber 170 through the proximal end of the delivery apparatus to displace the saline therein. The side port 174 is utilized to provide a reservoir for the therapeutic agent. Continued filling of the reservoir can cause the chamber 170 to be filled. As the therapeutic agent fills the chamber 170 the medical device absorbs and/or is coated and/or is loaded with the therapeutic agent. Once the medical device has absorbed and/or is coated and/or is loaded with the therapeutic agent, the apparatus can then be inserted into a patient's body for the deployment of the medical device. In the particular example shown in FIG. 12, a balloon catheter 176 is utilized to deploy a stent 178. However, other suitable delivery devices can also be utilized within the catheter 168 to deliver the medical device.

In another approach, the therapeutic agent is injected into the lumen of the delivery catheter through the port located at the proximal portion of the delivery apparatus to fill the lumen and coat and/or load the medical device with the therapeutic agent. In one design variation, the apparatus is configured without a separator 166. Therapeutic agent is injected through the distal portion of the apparatus to completely fill the lumen and coat and/or load the medical device with the therapeutic agent prior to inserting the delivery apparatus within the patient's body. Once the medical device is loaded with the therapeutic agent, the delivery apparatus can be inserted into the patient's body to deploy the medical device. Before the delivery apparatus is inserted into the patient's body, the user may infuse the lumen of the delivery apparatus with saline to flush out the excess therapeutic agent within the lumen.

It is believed that the approach utilized for the embodiments illustrated in, for example, FIG. 1-12, where the therapeutic agent is infused prior to or during the implantation alleviates problems associated with the shelf-life of such agents being different from the shelf-life of the delivery apparatus or the implantable medical device.

In another variation, the delivery apparatus includes a dual lumen delivery catheter. The delivery catheter includes a first lumen providing a conduit to allow the user to control the deployment of a medical device secured within the distal end of the delivery apparatus, and a second lumen providing a fluid conduit for transporting a therapeutic agent from the proximal end of the delivery apparatus to the distal end of the apparatus in order to coat and/or load the medical device with the therapeutic agent.

Figure 13:
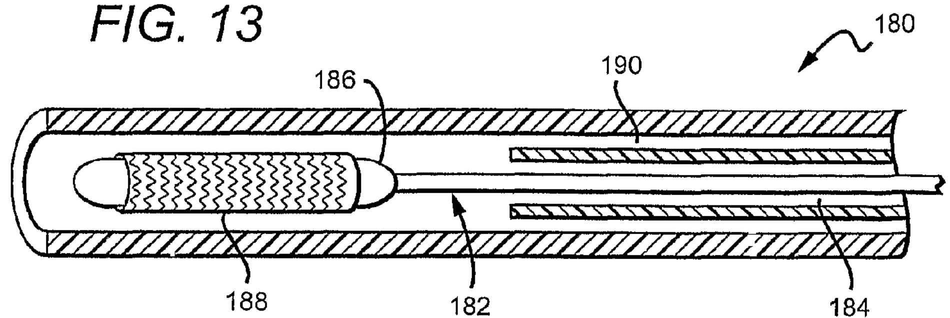
FIG. 13 illustrates another variation of a delivery apparatus comprising a dual lumen catheter. A first lumen provides a channel to allow the user to control the deployment of a medical device positioned within a chamber at the distal end of the apparatus. A second lumen provides a fluid conduit to allow the user to infuse a therapeutic agent into the distal chamber.
Figure 14:
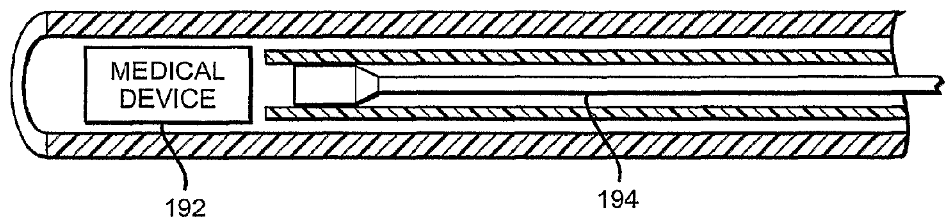
FIG. 14 illustrates another variation of a delivery apparatus with a dual lumen design. In this example, the apparatus is configured with coaxial lumens and a pusher element slidably positioned within the central lumen.

FIG. 13 illustrates the example where the delivery apparatus includes a coaxial dual lumen catheter 180 with a balloon catheter 182 slidably disposed within the central lumen 184. The balloon 186 on the balloon catheter 182 is shown in a deflated condition with a stent 188 positioned over the deflated balloon. A therapeutic agent can be injected down the outer lumen 190 to coat and/or load the stent 188 or stent-graft with the therapeutic agent. In one approach, the stent is coated with the therapeutic agent prior to the insertion of the delivery apparatus into the patient's body. In another approach, the stent 188 is coated with the therapeutic agent while the delivery apparatus is inserted within the body of the patient. In yet another approach, a therapeutic agent is injected down the outer lumen 190 and then suctioned up the central lumen 184 to induce a flow of the therapeutic agent over the medical device positioned in the distal end of the delivery apparatus to facilitate coating and/or loading of the medical device with the therapeutic agent. FIG. 14 illustrates another example, in which a medical device 192 is positioned within a chamber at the distal end of the delivery apparatus, and a pusher element 194 is positioned within the central lumen of the delivery apparatus.

Figure 15:
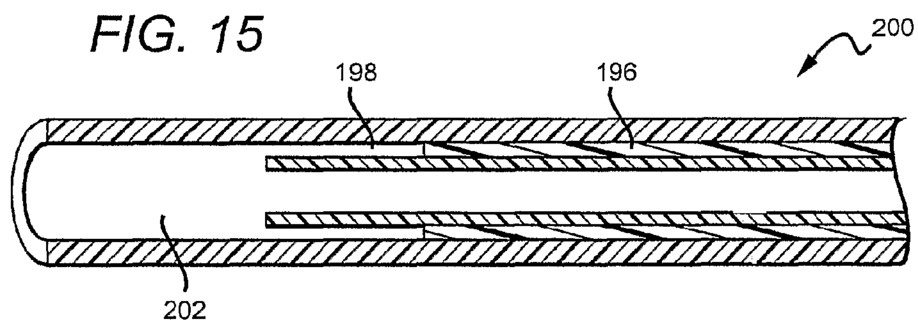
FIG. 15 illustrates another variation of a delivery apparatus with a coaxial lumen design. An insert is slidably positioned within the outer lumen to serve as a suction mechanism to draw a therapeutic agent into the distal portion of the apparatus.
Figure 16:
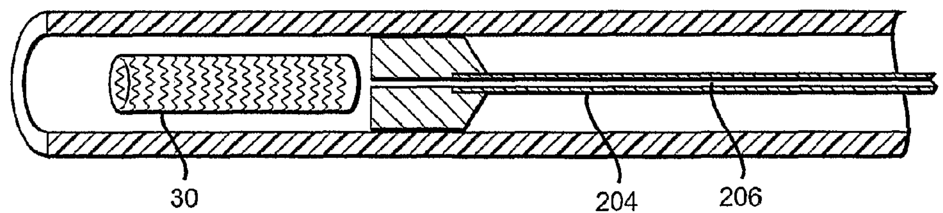
FIG. 16 illustrates another variation of a delivery apparatus where a pusher element for deploying the medical device is configured with a lumen. The lumen may be utilized for infusing the distal portion of the apparatus with a therapeutic agent.

FIG. 15 illustrates another variation, in which an insert 196 is positioned within the outer lumen 198 of the dual lumen delivery apparatus 200. The displacement of the insert 196 allows the user to generate a suction to induce the therapeutic agent to enter the distal chamber 202 and coat a medical device positioned therein. The insert 196 may also be displaced proximally to create a reservoir at the distal portion of the outer lumen for containing a therapeutic agent. Later, the insert can be advanced distally to eject the therapeutic agent into the chamber to coat the medical device. In another example, as shown in FIG. 16, the pusher element 204 is configured with a lumen 206, such that the user can inject a therapeutic agent down the shaft of the pusher element to infuse the proximal section of the delivery catheter with a therapeutic agent. In one application, the lumen 206 of the pusher element is pre-filled with a therapeutic agent. When the user is ready to coat the medical device 30 housed within the distal end of the delivery catheter, the therapeutic agent is ejected out of the distal end of the pusher element 204.

FIG. 17 shows another example where a first catheter 208 is slidably disposed within the lumen of a second catheter 210. The lumen of the first catheter 208 to can be utilized to infuse a therapeutic agent to coat a medical device 30 positioned within the lumen of the second catheter 210. To deploy the medical device 30, the first catheter is advanced distally to eject the medical device 30. In one variation, the inner catheter 212 further includes a cap 214 positioned at the distal end of the catheter 212, as shown in FIG. 18. An elongated wire 216 is slidably positioned within the lumen of the inner catheter 212. A stopper 218 is connected to the distal end of the elongated wire 216. The displacement of the elongated wire 216 in the proximal direction moves the stopper 218 proximally and creates a chamber 220 within the lumen of the inner catheter 212. In one application, the stopper can be displaced to generate a suction. The suction draws a therapeutic agent into the distal end of the outer catheter to coat the medical device 30 positioned therein. In another application, the stopper can be displaced to create a reservoir that is pre-loaded with a therapeutic agent. When the user is ready to coat the medical device with the therapeutic agent, the stopper is then advance distally to release the therapeutic agent into the lumen of the outer catheter. Optionally, a valve is provided over the orifice of the cap positioned at the distal end of the inner catheter.

In another aspect, the delivery apparatus includes a delivery catheter 224 and a pusher element 226 slidably disposed within the lumen of the delivery catheter, as shown in FIG. 19A. The pusher element 226 includes an elongated wire 228 coupled to a pusher pad 230. The pusher pad 230 includes flanges 232 that extend radially into the corresponding grooves 234 on the inner lumen wall of the delivery catheter 224, as shown in FIG. 19B. The flanges 232 ensure that the pusher pad engages the medical device, which is housed within the distal end of the delivery apparatus 2, when the pusher pad 230 is advanced distally to eject the medical device. This configuration may be particularly useful for engaging a medical device that has a large center opening (e.g., stent, etc.). In one variation, the pusher pad 230 is further configured with channels to allow fluids to flow through the pusher pad, such that fluids infused through the proximal end of the catheter can reach the distal end of the catheter. In another variation, the pusher pad 230 includes a reservoir that contains a therapeutic agent. In yet another variation, the pusher element 226 includes a flexible rod connected to the pusher pad. The flexible rod includes a lumen, such that a fluid injected into the proximal end of the flexible rod flows out at the distal end of the pusher pad.

FIG. 20 illustrates another variation of a delivery apparatus according to the present invention, comprising an elongated insert 240 slidably disposed within the lumen of a catheter 242. A distal end 241 of the elongated insert 240 is inserted through a medical device 30 (e.g., stent), which is positioned in the distal lumen of the catheter 242. The elongated insert 240 includes a lumen 244 such that fluids can be transported down the shaft of the elongated insert 240. An orifice 246 is positioned at the distal portion of the elongated insert 240 such that fluids injected into the lumen 244 of the elongated insert 240 can exit the elongated insert through the orifice 246. In one variation, the elongated insert is provided with a plurality of orifices 246, which are distributed on the circumferential surface at the distal section of the elongated insert 240. The plurality of orifices 246 may be configured such that fluids ejected out of theses orifices can distributed over the length of the stent, which is positioned around the distal section of the insert. In one variation, the orifices 246 are distributed over the distal section of the elongated insert in a spiral pattern. An optional flange or disk 248 may be attached to the shaft of the elongated insert 240, such that the advancement of the elongated insert 240 in the distal direction causes the flange 248 to engage the medical device 30 and force the medical device out of the distal end 250 of the delivery catheter 242. In one variation, the flange 248 is configured with through holes 252 (FIG. 20), such that fluid injected into the proximal end of the delivery catheter lumen can travel past the flange and enter the distal section of the catheter lumen. In another variation, the elongated insert is configured such that it can be rotated axially in relation to the catheter 242. The axial rotation of the elongated insert can be used to facilitate the distribution of the therapeutic agent over the medical device.

In the above application, a therapeutic agent is injected into the proximal end of the elongated insert 240. The therapeutic agent travels down the lumen 244 in the shaft of the elongated insert 240 toward the distal end 241 of the elongated insert. The therapeutic agent exits the orifices 246 on the distal section of the elongated insert 240 and coats the stent 30 positioned around the distal section of the elongated insert 240. Once the stent 30 is coated with the therapeutic agent, the elongated insert 240 can be advanced distally to deploy the stent 30. In another variation, the elongated insert is configured for coating the stent with a therapeutic agent only. Once the stent is coated with the therapeutic agent, the elongated insert is removed, and a pusher element is inserted into delivery catheter to deploy the stent.

FIG. 21A illustrates another variation of a delivery apparatus 2 comprising a dual lumen catheter 260. A medical device 30 (e.g., stent, etc.) is slidably positioned in inner lumen 262 of the catheter 260 at the distal section of the catheter. The wall between the inner 262 and the outer 264 lumen includes a plurality of orifices 266 at the distal section thereof to enable fluid communication between the inner lumen 262 and the outer 264 lumen, as shown in FIG. 21B. A therapeutic agent can be injected into the outer lumen at the proximal end of the catheter. The therapeutic agent flows distally through the outer lumen 264 and through the orifices 266 to enter into the inner lumen 262 and into contact with the medical device 30. If the medical device 30 includes, an absorption member, a porous member, or a sponge-like material, the therapeutic agent can be absorbed into the body of the medical device. Once the medical device is coated and/or loaded with the therapeutic agent, it can then be deployed within the patient's body.

It should be noted that the various embodiments described herein can be utilized with a reservoir located in the catheter or a reservoir external to the catheter.

FIG. 22 shows another variation where the delivery apparatus 2 further includes a pusher element 268 for deploying the medical device 30 from the inner lumen 270 of the catheter 272. In this particular example, a medical device (e.g., a vascular filter 294) is loaded in the inner lumen 270 of the dual lumen catheter. In this embodiment, the distal end of the catheter can be configured with one or more slots 276 to separate the appendages 278, if any, on the medical device 30, such as a vessel filter having a plurality of legs, and prevent the appendages from entangling with each other.

FIG. 23 illustrates another variation where the delivery apparatus 2 includes a balloon catheter 280 carrying a stent 282 slidably disposed within a dual lumen catheter 284. A first port 286, located on the proximal section of the catheter, is configured for accessing the inner lumen 288, while a second port 290, also located on the proximal section of the catheter, is configured for accessing the outer lumen 292 of the catheter. A therapeutic agent can be injected into either the outer lumen 292 or the inner lumen 288 to coat and/or load the stent 282 positioned over the balloon on the balloon catheter 280. In one approach, the therapeutic agent is injected through one lumen while being extracted through a section in the second lumen. As a result, a flow of therapeutic agent is generated over the stent for coating the surface of the stent with the therapeutic agent. Optionally, a cap 294 may be provided to cover the distal end of the catheter 284 when the stent 282 is being coated within the inner lumen of the catheter 284. In one variation, the cap includes a polymeric layer, which provides a seal around the tip of the catheter, and which is configured for placement over the tip of the catheter. In one example, two O-rings 296, 298 are placed within the inner lumen of the cap 294 to provide the seal. Additionally, the cap 294 may also be utilized with other embodiments described herein.

FIG. 24 illustrates yet another variation of a delivery apparatus 2 comprising a pusher element 300 slidably disposed in the inner lumen of a dual lumen catheter 302. In this variation, the pusher element 300 includes a lumen 304 to provide fluid communication through the length of the pusher element.

In another aspect of the invention, a medical device is coated or infused with a therapeutic agent under pressure while positioned in a delivery apparatus. The delivery apparatus may be provided to the end user (e.g., surgeon performing the implant procedure, etc.) with the medical device pre-loaded in the delivery apparatus. In another variation, the end user has to load the medical device in the delivery apparatus prior to implantation. With the medical device loaded in the delivery apparatus, a therapeutic agent, which is pressured in a container, is infused or injected into the chamber of the delivery apparatus housing the medical device. The therapeutic agent can be injected into the delivery apparatus in various forms including, but not limited to, mist, spray, foam, liquid stream, or gel stream. Various delivery mechanisms (e.g., spray pump, aerosol can, pressure pump, etc.) can be utilized to infuse the therapeutic agent into the delivery apparatus to coat and/or load the medical device therein.

Figure 25:
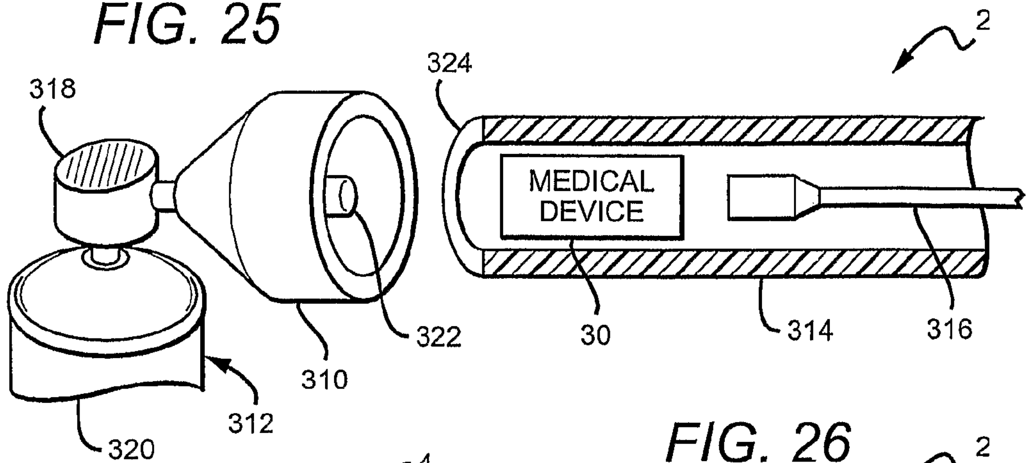
FIG. 25 illustrates a method for coating and/or infusing an implantable medical device under pressure, while the device is loaded within a delivery apparatus.

Referring to FIG. 25, an adaptor 310 is provided with interfaces to couple a therapeutic agent injection mechanism 312 (e.g., a pressure generating source configured to eject the therapeutic agent) to the distal end of a delivery apparatus. In one variation, the delivery apparatus 2 includes a catheter 314 with a deployment mechanism 316 positioned within the lumen of the catheter. A medical device 30 is positioned in a chamber within the distal section of the catheter lumen. The adaptor 310 is connected to the nozzle 318 of an aerosol can 320, which carries a therapeutic agent. The distal end of the adaptor 310 has an interface that receives the nozzle of the aerosol can, and the proximal end of the adaptor has an interface 322 that receives the distal end 324 of the catheter 314 and forms a seal around the catheter tip. The user inserts the distal end 324 of the catheter 314 into the adaptor 310. The lever on the aerosol can is then depressed to infuse the therapeutic agent into the lumen of the catheter to coat and/or load the implantable medical device with the therapeutic agent.

Figure 26:
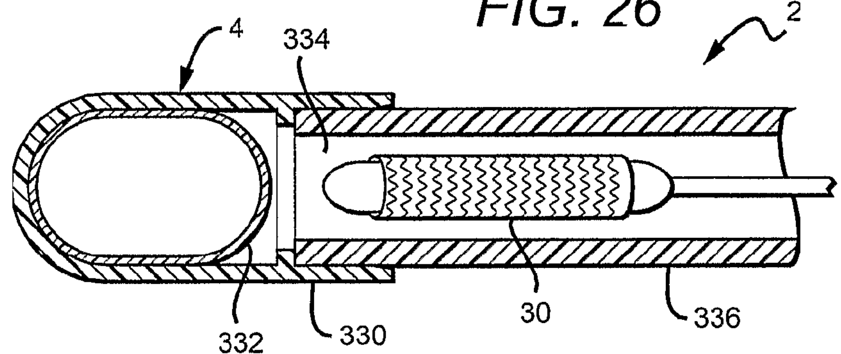
FIG. 26 illustrates another variation of a delivery apparatus comprising a reservoir of therapeutic agent that can be attached to the distal end of the delivery catheter to coat/infuse the medical device positioned within the delivery catheter. In this particular example, the reservoir includes a pressurized capsule loaded with a therapeutic agent. When the integrity of the capsule is included, the therapeutic agent is released into the lumen of the delivery catheter.

In another aspect of the invention, a reservoir containing a therapeutic agent is configured for attachment onto the distal end of the delivery apparatus (e.g., delivery catheter, etc.). Once the reservoir is connected to the distal end of the catheter, the user can release the therapeutic agent into the lumen of the delivery apparatus to coat and/or load the medical device located in the delivery apparatus. Referring to FIG. 26, a reservoir 4, including a cap 330 containing a capsule 332 filled with a therapeutic agent is inserted over the distal end of the delivery apparatus 2. The user applies a pressure over the cap 330 to break the capsule 332 and release the therapeutic agent. The released therapeutic agent flows into the lumen 334 of the catheter 336 and coats the medical device 30 positioned therein. In one variation, the compartment within the capsule is pressurized.

In another variation, the delivery apparatus is provided to the user with a reservoir of a therapeutic agent connected to the distal end of the catheter. A medical device is pre-loaded in the delivery apparatus. When the user is ready to insert the medical device into the patient, the user releases the therapeutic agent from the reservoir to coat and/or load the medical device. In one variation, the reservoir is pressurized to facilitate the ejection of the therapeutic agent from the reservoir. Once the coating/loading process is completed, the user then disconnects the reservoir from the distal end of the delivery apparatus. With the reservoir removed, the user can insert the delivery apparatus into the patient and deploy the medical device.

Figure 27:
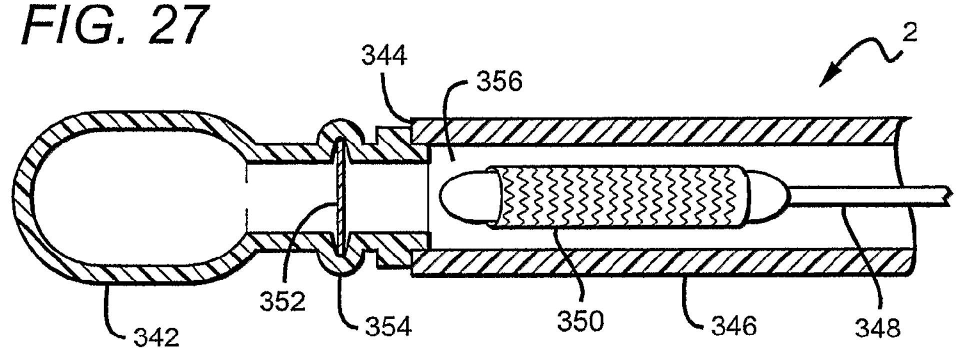
FIG. 27 illustrates yet another variation of a delivery apparatus including a breakaway reservoir attached to the distal end of a delivery catheter. Once the therapeutic agent within the breakaway reservoir has been released into the lumen of the delivery catheter, the user can detach the breakaway reservoir.

A container can be attached to the distal end of a delivery apparatus. A valve can be provided on the container to control the outflow of a therapeutic agent retained within the reservoir. To coat the medical device, the user releases the valve and allows the therapeutic agent to flow into the lumen of the delivery apparatus. Once the medical device is coated with the therapeutic agent, the container is detached from the distal end of the delivery apparatus. In another example, a delivery apparatus includes a capsule 342 containing a therapeutic agent connected to the distal end 344 of a delivery catheter 346, as shown in FIG. 27. A balloon catheter 348 carrying a compressed stent 350 is slidably disposed within the lumen of the delivery catheter 346. The compartment within the capsule 342 is pressurized, such that once the valve or barrier 352 sealing the capsules opening is compromised, the therapeutic agent will be forced out of the capsule 342 due to the pressure. To coat the stent 350 on the balloon catheter 348, the user presses down on the neck 354 of the capsule to break the barrier 352 sealing the proximal opening of the capsule. Once the barrier 352 has been cracked, the therapeutic agent flows out of the capsule 342 and into the lumen 356 of the delivery catheter 346. Once the stent 350 is coated with the therapeutic agent, the user bends the capsule 342 relative to the delivery catheter 346, and breaks the capsule 342 off the delivery catheter 346. With the capsule removed, the distal end of the delivery catheter along with the stent and the balloon catheter can be inserted into an introducer sheath 346 and into a patient's body. Once the balloon catheter is positioned in the desired location within the patient, the delivery catheter is retracted to expose the stent. The balloon on the balloon catheter is then inflated to deploy the stent.

In another variation, the delivery apparatus includes a delivery catheter including a plurality of orifices positioned on the circumferential surface at a distal section of the delivery catheter. The user can infuse or introduce a therapeutic agent through these orifices to coat and/or load a medical device located in the lumen of the delivery catheter. For example, the delivery catheter along with a medical device, which is secured within the lumen of the catheter, may be dipped into a liquid therapeutic agent or placed into a pressurized chamber filled with a therapeutic agent. The therapeutic agent is diffused through the orifices in the delivery catheter to coat and/or load the medical device.

Figure 28:
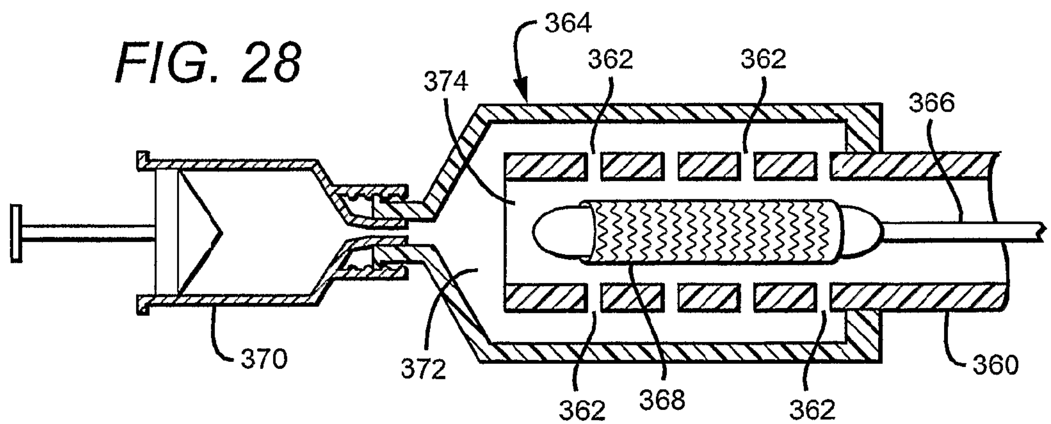
FIG. 28 illustrates another variation of a delivery apparatus comprising a delivery catheter with orifices on the circumferential surface, such that pressurized therapeutic agent can be infused into the lumen of the delivery catheter through these orifices. In the example shown in FIG. 28, an optional adaptor is provided to assist the user in injecting a therapeutic agent through circumferentially positioned orifices.

FIG. 28 illustrates one example, where a delivery catheter 360 including a plurality of circumferential orifices 362 is inserted into the proximal end of an adaptor 364. A balloon catheter 366 carrying a medical device is disposed within the lumen of the delivery catheter 360. The medical device (e.g., stent 368) is aligned within the distal portion of the catheter, such that the orifices surround the medical device. A syringe 370 filled with a therapeutic agent is attached to the distal end of the adaptor 364. The user injects the therapeutic agent into the chamber 372 within the adaptor. As the chamber 372 is filled with the therapeutic agent, the therapeutic agent is forced into the lumen of the catheter 360 through the distal opening 374 and the surrounding orifices 362. Once the stent 368 is coated with the therapeutic agent, the user can remove the syringe along with the adaptor.

Figure 29:
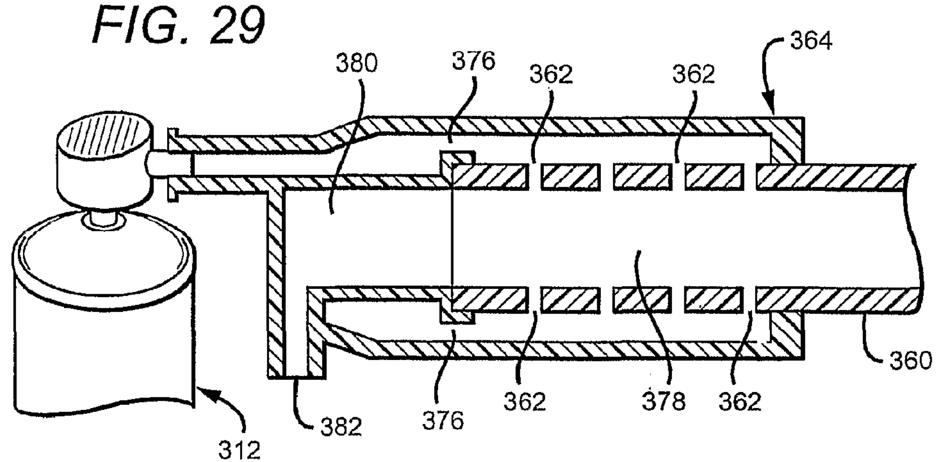
FIG. 29 illustrates another example for infusing the distal portion of a delivery catheter with a therapeutic agent. In this example, an adaptor is attached to the distal end of the delivery catheter, such that a pressurized therapeutic agent is infused into the delivery catheter through the circumferential orifices to coat the medical device within the lumen of the delivery catheter. The excess therapeutic agent is allowed to exit the distal end of the delivery catheter through an outlet on the adaptor.

FIG. 29 illustrates another variation of an adaptor 364 design. In this design, the adaptor includes an outer lumen and a central lumen. The outer lumen 376 of the adaptor 364 directs therapeutic agents into the lumen 378 of the catheter 360 through the circumferential orifices 362 on the distal section of the catheter. Excess therapeutic agent is allowed to flow out of the distal opening of the catheter and into the central lumen 380 of the adaptor 364. An opening 382 on the adaptor is provided to allow the excess materials to exit the adaptor 364.

In another aspect, a sponge-like or porous material is positioned close to the distal opening of a delivery apparatus. The sponge-like material can serve as a reservoir to retain a therapeutic agent. The therapeutic agent is pre-loaded or infused into the sponge-like material prior to the deployment of the medical device. As the medical device is propelled out of the distal opening of the delivery apparatus, the medical device glides over the sponge-like material, and the therapeutic agent is provided onto the surface of the medical device. The delivery of the therapeutic agent can be by wicking, or by squeezing of the porous material to force the agent on to the medical device.

Figure 30:
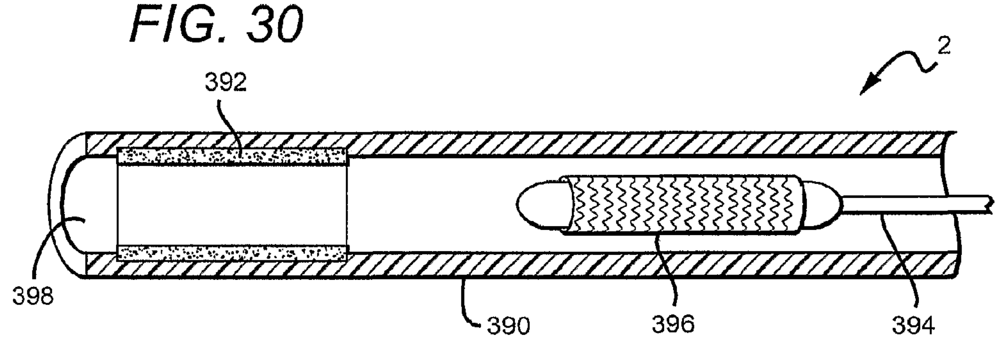
FIG. 30 illustrates yet another variation of a delivery apparatus comprising a sponge-like reservoir within the distal lumen of the apparatus. The sponge-like reservoir can be pre-loaded with a therapeutic agent, such that when the medical device is deployed through the distal end of the catheter, the sponge-like reservoir will coat or wick the circumferential surface of the device with the therapeutic agent. The example shown in FIG. 30 is configured to deploy a stent with a balloon catheter.

In one example, as shown in FIG. 30, the delivery apparatus 2 includes a delivery catheter 390 including a polymeric layer 392 with high absorbency attached to the inner wall of the catheter 390 at the distal portion of the catheter lumen. A balloon catheter 394 carrying a stent 396 is slidably disposed within the lumen 398 of the delivery catheter 390. The user first infuses the polymeric layer 392 with a therapeutic agent. The delivery catheter 390 along with the stent 396 and the balloon catheter 394 are then inserted into an introducer sheath positioned within the patient's body. Once the balloon catheter 394 is positioned in the desired location, the user can either advance the balloon catheter 394 relative to the delivery catheter 390, or retract the delivery catheter 390 relative to the balloon catheter 394, to deploy the stent. As the stent 396 passes over the polymeric layer 392, the therapeutic agent is delivered onto the surface of the stent 396.

Figure 31:
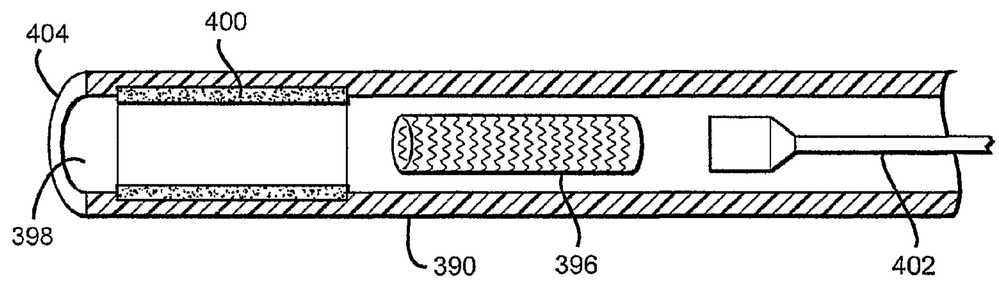
FIG. 31 illustrates another example of utilizing a delivery apparatus with a sponge-like reservoir. In this example, the apparatus is configured with a pusher element for deploying a stent.

In another example, the delivery apparatus includes a delivery catheter 390 with a sponge-like layer 400 positioned around the distal lumen section. A stent 396 is slidably positioned with the lumen of the catheter 390, as shown in FIG. 31. A pusher element 402 is position with the lumen 398 proximal of the stent 396. The user first infuses the sponge-like layer 400 with a therapeutic agent. Once the sponge-like layer 400 is infused with the therapeutic agent, the user may advance the stent 396 distally and position the stent within the sponge-like layer 400. Next, the delivery catheter 390 is inserted into the patient's body, and the stent 396 is deployed through the distal opening 404 of the delivery catheter 390. In another variation, the sponge-like layer in the delivery apparatus is pre-loaded with a therapeutic agent before the delivery apparatus is provided to the user.

In another aspect, the medical device configured for deployment with the deployment apparatus can include a coating to facilitate the retention of the therapeutic agent on the medical device. For example, a coating with affinity for binding a therapeutic agent may be implemented on a medical device. In one variation, a biocompatible polymer with affinity to one or more therapeutic agents can be coated on the surface of the medical device. In another example, a gelatin, a hydrogel, or other hydrophilic or hydrophobic polymers may be integrated in the medical device to absorb and/or retain the therapeutic agent. The polymeric layer can be configured to allow slow release of the therapeutic agent over time after the device has been deployed within the patient's body. Polymers which may be suitable for incorporating on a medical device as drug carrier include, but not limited to, Poly(urethanes), Poly(siloxanes), Poly(methyl methacrylate), Poly(vinyl alcohol), Poly(ethylene), Poly(vinyl pyrrolidone),Poly(2-hydroxy ethyl methacrylate), Poly (N-vinyl pyrrolidone), Poly(methyl methacrylate), Poly(vinyl alcohol), Poly(acrylic acid), Polyacrylamide, Poly (ethylene-co-vinyl acetate), Poly(ethylene glycol), Poly (methacrylic acid), Polylactides (PLA), Polyglycolides (PGA), Poly(lactide-co-glycolides) (PLGA), Polyanhydrides, Polyorthoesters. Other absorptive materials or scaffold with reservoir for retaining liquid that are well known to one skilled in the art may also be utilized on the medical device for retaining therapeutic agent.

In yet another aspect, methods for loading (e.g., infusing, absorbing, coating, etc.) a medical device with a therapeutic agent while the medical device is positioned in the lumen of the catheter is disclosed herein. In one example, the method includes providing a medical device, a therapeutic agent, and a delivery apparatus to a medical practitioner. The medical device, the therapeutic agent, and the delivery apparatus can be provided to the medical practitioner in an integrated packaging or as separate items. In one variation, the delivery apparatus and the medical device are provided in a single sterile package, and the therapeutic agent is provided in a separate container. The medical device can be pre-loaded in the delivery apparatus before packaging. Alternatively, the medical device can be provided as separated items in the packaging. The medical device and delivery apparatus integrated package can also be provided to the medical practitioner as a single use deposable system. The integrated packaging may minimize confusion in matching the appropriate delivery apparatus with the medical device. Once the medical device is implanted, the medical practitioner may dispose of the delivery apparatus. By packaging the therapeutic agent separately, the medical practitioner can selected the appropriate medication base on specific patient need and the requirements of the specific implant procedure. In some application, the therapeutic agent may need to be refrigerated or store in an environmental control chamber. Storing the therapeutic agent separately from the medical device and the delivery apparatus may maximize storage efficiency.

In another variation, the therapeutic agent is packaged with the delivery apparatus, and the medical device is provided as a separate unit. This approach may allow the manufacturer to match up a therapeutic agent with the appropriate delivery apparatus. The medical practitioner can then select the appropriate medical device for deployment with the delivery apparatus. For example, the medical practitioner may select the medical device from a group of devices based on type, functional capability, size, material property, etc. In yet another variation, the therapeutic agent is provided in the same packaging as the medical device, and the delivery apparatus is provided separately. In some application, a particular therapeutic agent may be especially suitable for use with a specific medical device. Thus, it would be convenient for the manufacture to package the therapeutic agent with medical device. Furthermore, it may also be useful to package an interface (e.g., a universal syringe adaptor, aerosol can adaptor, etc.) and/or a therapeutic agent loading mechanism (e.g., a syringe, etc.) with the delivery apparatus. In certain application, the manufacture can also provide a medical device loading instrument along with the delivery device to assist the medical practitioner to insert the medical device into the delivery apparatus.

As discussed above, the medical device can be provided to the medical practitioner preloaded in the delivery apparatus or it can be provided to the medical practitioner as a two separate items, requiring the medical practitioner or his assistant to load the medical device into the delivery apparatus prior to deployment. The therapeutic agent may be provided to the medical practitioner as an integrated package having the therapeutic agent along with the delivery apparatus and/or the medical device. The therapeutic agent, the medical device, and the delivery apparatus, may also be provided to the medical practitioner as individual units.

With the device loaded in the delivery apparatus, the therapeutic agent is infused into the delivery apparatus to load the medical device with the therapeutic agent. For example, a syringe may be utilized to inject the therapeutic agent into the delivery apparatus either from the proximal end or the distal end of the delivery apparatus, depending on the design of the specific delivery apparatus. A syringe adaptor may be provided for coupling the syringe with the delivery apparatus. In one variation, the therapeutic agent is preloaded into a syringe. The user can remove a cap on the syringe and insert the tip of the syringe into the distal opening of the delivery apparatus. The therapeutic agent is then injected into the lumen of the delivery apparatus to load the medical device with the therapeutic agent. In another variation, the therapeutic agent is provided within a container. A syringe with the needle can be used to extract the therapeutic agent out of its container and into the syringe. The needle on the syringe can then be inserted into the distal end of the delivery apparatus to inject the therapeutic agent. Alternatively, the needle can be removed, and the tip of the syringe inserted into the distal end of the delivery apparatus to infuse the therapeutic agent. In another variation, an adapter is provided to couple the syringe to the distal tip of the delivery apparatus to assist with the injection of the therapeutic agent into the delivery apparatus. As one skilled in the art having the benefit of this disclosure would appreciate, the syringe could also be utilized to inject therapeutic agent into the proximal end of the delivery apparatus.

In another example, an aerosol can carrying the therapeutic agent is couple to the delivery apparatus (either directly or through an adaptor) to infuse the inner chamber of the delivery apparatus, which holds the medical device. In one variation, the therapeutic agent is loaded onto the medical device, which is positioned in the delivery apparatus, before the delivery apparatus is inserted into the patient's body. In another variation, the therapeutic agent is loaded onto the medical device after the delivery apparatus, along with the medical device, has already been inserted into the patient's body.

In yet another example, the therapeutic agent is provided to the medical practitioner in a pump dispenser (e.g., spray pump, microsprayer, lotion pump, trigger sprayer pump, pressure sprayer, mist sprayer, etc.). With the medical device positioned in the deployment apparatus, the medical practitioner dispenses the therapeutic agent out of the pump dispenser and into the delivery apparatus to load the medical device with the therapeutic agent. An adaptor can be used to facilitate the transfer of the therapeutic agent from the pump dispenser into the delivery apparatus. In addition, the method for loading the medical device positioned in the delivery apparatus can also include the step of pressurizing the pump dispenser or other container containing the therapeutic agent, prior to injecting or spraying the therapeutic agent into the delivery apparatus to load the medical device with the therapeutic agent. The pressurizing step may include activating a pump to increase the pressure inside of a canister containing the therapeutic agent. In another variation, the pressurizing step comprises shaking a canister (e.g., an aerosol canister, etc.) containing the therapeutic agent to increase the pressure in the canister.

One skilled in the art having the benefit of this disclosure would appreciate that some variations of the delivery apparatus disclosed herein may be applicable for simultaneous delivery of a therapeutic agent and a medical device into a pre-selected site within a patient's body. The medical device chamber of the delivery apparatus may be pre-loaded with a therapeutic agent, such that the therapeutic agent and the medical device can be introduced into the pre-selected site within the patient's body simultaneously. It should also be appreciated that during the deployment of the medical device, a therapeutic agent may also be injected through a drug lumen in the delivery apparatus to infuse the deployment site with a therapeutic agent.

As discussed above, the medical device disclosed herein may be configured to serve as a carrier to deliver a therapeutic agent onto a target site within a patient's body. For example, a method utilizing a medical device as a gene therapy delivery platform is described below. The delivery apparatus is configured to deliver the medical device, which carries stem cells or a gene therapy agent, to a pre-selected location within the patient's body. In one variation, the medical device includes a stent covered with a polymeric layer configured to absorb proteins, nucleic acid chains and/or other large molecules is loaded in the delivery apparatus. In one variation, while the stent is loaded in the delivery apparatus, Vascular Endothelial Growth Factor-2 (VEGF-2) in the form of naked DNA plasmid, a nonviral vector, is loaded into the polymeric layer on the stent. With the VEGF-2 loaded on the stent, the delivery apparatus is inserted into the patient's body to deploy the stent at the pre-selected site. In another approach, the gene therapy agent is loaded in a reservoir in the distal portion of the delivery apparatus. Immediately prior to or during the deployment of the stent, the gene therapy agent is then released into the lumen of the delivery apparatus.

One skilled in the art having the benefit of this disclosure would also appreciate that the delivery apparatus disclosed herein is not limited for loading and/or coating a medical device with a therapeutic agent for deployment inside a patient's body. Various other chemicals, biochemical, and biologics may also be coated and/or loaded onto a medical device for delivery into a patient's body.

While the invention has been described in terms of particular variations and illustrative figures, those skilled in the art will recognize that the invention is not limited to the variations or figures described. In addition, where methods and steps described above indicate certain events occurring in certain order, those skilled in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A drug loading system, comprising:

a medical device delivery apparatus having a distal portion and a distal tip at a distal end of the distal portion;

a medical device disposed in the distal portion;

an injection mechanism comprising an aerosol can wherein the aerosol can contains a therapeutic agent; and an adaptor coupling the injection mechanism directly to the distal end of the delivery apparatus and directing the therapeutic agent from the injection mechanism into the distal portion of the delivery apparatus to coat or load the medical device.

2. The drug loading system according to claim 1, wherein the therapeutic agent comprises a material selected from a group consisting of a stem cell, a gene therapy agent, a protein, a nucleic acid chain, a growth factor, and combinations thereof.

3. The drug loading system according to claim 2 wherein the adaptor comprises a first lumen for directing the therapeutic agent into the delivery apparatus, and a second lumen for directing an excess portion of the therapeutic agent out of a lumen of the delivery apparatus.

4. The drug loading system according to claim 3, wherein the adaptor further comprises an interface for receiving the distal tip.

5. A drug loading system, comprising:

a medical device delivery apparatus having a distal portion and a distal tip at a distal end of the distal portion;

a medical device disposed in the distal portion;

an injection mechanism containing a therapeutic agent; and an adaptor coupling the injection mechanism directly to the distal end of the delivery apparatus and adapted to direct the therapeutic agent from the injection mechanism through the distal tip into the distal portion of the delivery apparatus to coat or load the medical device.

6. The drug loading system according to claim 5, wherein the adaptor further comprises an interface for receiving the distal tip.

7. The drug loading system according to claim 5, wherein the therapeutic agent comprises a material selected from a group consisting of a stem cell, a gene therapy agent, a protein, a nucleic acid chain, a growth factor, and combinations thereof.

8. The drug loading system according to claim 7, wherein the adaptor comprises a first lumen for directing the therapeutic agent into the delivery apparatus, and a second lumen for directing an excess portion of the therapeutic agent out of a lumen of the delivery apparatus.

9. The drug loading system of claim 8, wherein the injection mechanism comprises an aerosol can.

10. The drug loading system of claim 9, further comprising an interface adapted to receive the distal tip.

11. A method for implanting a medical device, comprising:

supplying the drug loading system of claim 5;

disposing a portion of the medical device in the delivery apparatus;

and releasing the therapeutic agent from a reservoir located in the injection mechanisim to coat or load the medical device.

12. The method according to claim 11, further comprising the steps of inserting the delivery apparatus into a patient's body, and deploying the medical device into the patient's body.

13. The method according to claim 11, wherein the reservoir is pressurized prior to the releasing step.

14. The method according to claim 11, wherein the reservoir is positioned in the delivery apparatus.

15. The method according to claim 11, wherein the reservoir is separate from the delivery apparatus, the method further comprising the step of coupling the reservoir to the delivery apparatus before releasing the therapeutic agent from the reservoir to load the medical device.

16. The method according to claim 15, further comprising the steps of providing the delivery apparatus to a medical practitioner, and providing a container comprising the reservoir to said medical practitioner.

* * * * *